US010292589B2

(12) United States Patent
Wang et al.

(10) Patent No.: US 10,292,589 B2
(45) Date of Patent: May 21, 2019

(54) ACOUSTIC-ASSISTED ITERATIVE WAVE FORM OPTIMIZATION FOR DEEP TISSUE FOCUSING

(75) Inventors: Ying Min Wang, Pasadena, CA (US); Changhuei Yang, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 326 days.

(21) Appl. No.: 13/237,796

(22) Filed: Sep. 20, 2011

(65) Prior Publication Data

US 2012/0070817 A1    Mar. 22, 2012

Related U.S. Application Data

(60) Provisional application No. 61/384,660, filed on Sep. 20, 2010.

(51) Int. Cl.
*A61B 5/00* (2006.01)
*G01N 21/47* (2006.01)
*G01N 21/49* (2006.01)
*G01N 21/65* (2006.01)
*G01N 21/17* (2006.01)

(52) U.S. Cl.
CPC ....... *A61B 5/0059* (2013.01); *G01N 21/1717* (2013.01); *G01N 21/47* (2013.01); *G01N 21/49* (2013.01); *G01N 21/65* (2013.01); *G01N 2021/1727* (2013.01); *G01N 2021/4709* (2013.01)

(58) Field of Classification Search
USPC ........................................................ 600/407
See application file for complete search history.

(56) References Cited

U.S. PATENT DOCUMENTS

| 4,866,781 | A |   | 9/1989 | Borken et al. |
|---|---|---|---|---|
| 4,928,695 | A |   | 5/1990 | Goldman et al. |
| 4,945,239 | A |   | 7/1990 | Wist et al. |
| 5,521,930 | A | * | 5/1996 | Suni et al. ..................... 372/13 |
| 5,760,388 | A |   | 6/1998 | Swandic |
| 6,172,354 | B1 | * | 1/2001 | Adan et al. .................. 250/221 |
| 6,216,540 | B1 | * | 4/2001 | Nelson et al. ................. 73/633 |

(Continued)

OTHER PUBLICATIONS

Im Vellekoop and AP Mosk, "Focusing coherent light through opaque strongly scattering media," 2007, Optics Letters, vol. 32, No. 16, pp. 2309-2311.*

(Continued)

*Primary Examiner* — James M Kish
(74) *Attorney, Agent, or Firm* — Gates & Cooper LLP

(57) ABSTRACT

A method, apparatus, and article of manufacture for irradiating one or more targets within a sample with electromagnetic (EM) radiation. One or more targets within the sample are controllably defined with an acoustic field. The sample is irradiated with input EM radiation having an input wavefront. An amount of frequency shifted EM radiation is detected, wherein at least some of the input EM radiation that passes through the acoustic field at the targets is shifted in frequency to form the frequency shifted EM radiation. The input wavefront is modified, using feedback comprising the amount of the frequency shifted EM radiation that is detected, into a modified wavefront. The sample is irradiated using the input EM radiation comprising the modified wavefront, and the process is repeated as desired.

25 Claims, 10 Drawing Sheets

(56) References Cited

U.S. PATENT DOCUMENTS

| | | | |
|---|---|---|---|
| 6,289,230 B1* | 9/2001 | Chaiken et al. | 600/322 |
| 6,334,846 B1* | 1/2002 | Ishibashi et al. | 600/439 |
| 6,385,474 B1* | 5/2002 | Rather | A61B 8/08 128/920 |
| 6,537,829 B1* | 3/2003 | Zarling et al. | 436/514 |
| 7,330,746 B2* | 2/2008 | Demuth et al. | 600/322 |
| 7,416,535 B1* | 8/2008 | Kenny | 601/2 |
| 2003/0020923 A1* | 1/2003 | Dubois et al. | 356/502 |
| 2005/0074779 A1* | 4/2005 | Vo-Dinh | 435/6 |
| 2005/0158059 A1* | 7/2005 | Vaananen | 398/183 |
| 2006/0004306 A1* | 1/2006 | Altshuler et al. | 601/3 |
| 2006/0058685 A1* | 3/2006 | Fomitchov et al. | 600/476 |
| 2006/0266917 A1* | 11/2006 | Baldis et al. | 250/200 |
| 2008/0228178 A1* | 9/2008 | Van Hal et al. | 606/9 |
| 2008/0249526 A1* | 10/2008 | Knowlton | 606/45 |
| 2009/0138215 A1* | 5/2009 | Wang et al. | 702/48 |
| 2009/0297455 A1* | 12/2009 | Suijver et al. | 424/9.5 |
| 2010/0015576 A1* | 1/2010 | Altshuler et al. | 433/218 |
| 2010/0225913 A1* | 9/2010 | Trainer | G01N 15/0205 356/338 |
| 2010/0231909 A1* | 9/2010 | Trainer | G01B 11/08 356/336 |
| 2011/0071402 A1* | 3/2011 | Masumura | G01N 21/4795 600/476 |

OTHER PUBLICATIONS

Cui, M., "A high speed wavefront determination method based on spatial frequency modulations for focusing light through random scattering media," Optics Express, Feb. 14, 2011, vol. 19, No. 4, 2989.

Cui, M. et al., "Parallel wavefront optimization method for focusing light through random scattering media," Optics Letters, vol. 36, No. 6, Mar. 15, 2011, 870.

Gross, M. et al., "Detection of the tagged or untagged photons in acousto-optic imaging of thick highly scattering media by photorefractive adaptive holography," Eur. Phys. J. E 28, 173-182 (2009).

Gross, M. et al., "Shot-noise detection of ultrasound-tagged photons in ultrasound-modulated optical imaging," Optics Letters, vol. 28, No. 24, Dec. 15, 2003, 2482.

Kothapalli, S. et al., "Ultrasound-modulated optical microscopy," Journal of Biomedical Optics 13(5), 054046 (Sep./Oct. 2008).

McDowell, E. et al., "Turbidity suppression from the ballistic to the diffusive regime in biological tissues using optical phase conjugation," Journal of Biomedical Optics 15(2), 025004 (Mar./Apr. 2010).

Popoff, S. et al., "Measuring the transmission matrix in optics: An approach to the study and control of light propagation in disordered media," Physic Review Letters, 104, 100601 (2010).

Sakadzic, S. et al., "High-resolution ultrasound-modulated optical tomography in biological tissues," Optics Letters, vol. 29, No. 23, Dec. 1, 2004, 2770.

Vellekoop, I. et al., "Focusing coherent light through opaque strongly scattering media," Optics Letters, Aug. 15, 2007, vol. 32, No. 15, 2309.

Vellekoop, I. et al., "Universal optimal transmission of light through disordered materials," Physical Review Letters, 101, 120601 (2008).

Wang, F., "Wavefront sensing through measurements of binary aberration modes," Applied Optics, May 20, 2009, vol. 48, No. 15, 2865.

Wang, L., "Ultrasound-mediated biophotonic imaging: A review of acousto-optical tomography and photo-acoustic tomography," Disease Markers 19 (2003, 2004) 123-138.

Yamaguchi, I. et al., "Phase-shifting digital holography," Optics Letters, vol. 22, No. 16, Aug. 15, 2007, 1268.

Olympus, High Frequency V3330, http://shop.olympus-ims.com/en/shop/item/269-productId.570437674_269-catId.562036984.html.

Navigator Modular Q-Switched Lasers, http.//www.newport.com/Navigator-Modular-Q-Switched-Lasers/501257/1033/info.aspx.

PCO.Edge, http://www.pco.de/categories/scmos-cameras/pcoedge/.

MatLab Central, http://mathworks.com/matlabcentral/fileexchange/11112.

PCT International Search Report and Written Opinion dated Jun. 29, 2011 for PCT Application No. PCT/US2010/056270.

Vellekoop, IM, et al., "Demixing light paths inside disordered metamaterials", Optics Express, Jan. 7, 2008, pp. 67-80, vol. 16, No. 1.

Wenner, Melinda, "The most transparent research", Nature Medicine, Oct. 2009, pp. 1106-1109, vol. 15, No. 10.

* cited by examiner

Illustration of a method of reference [1]

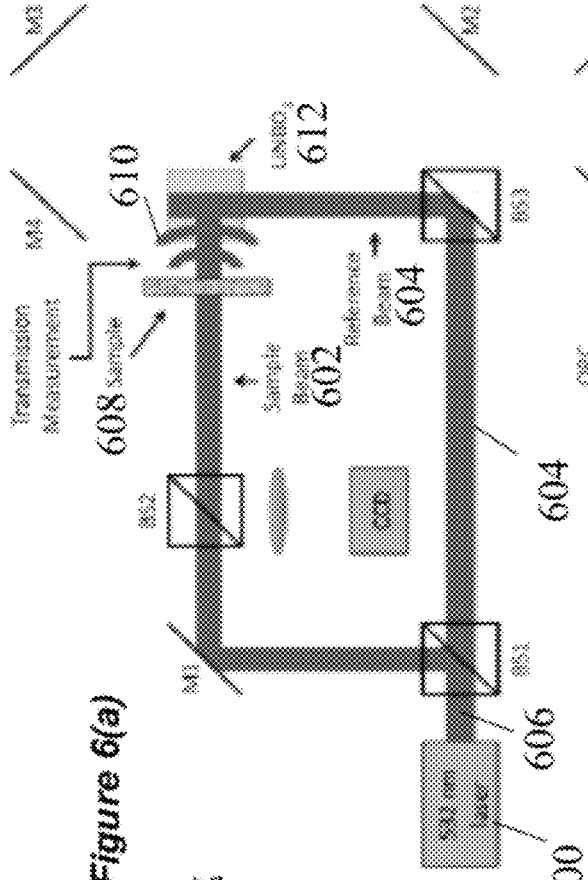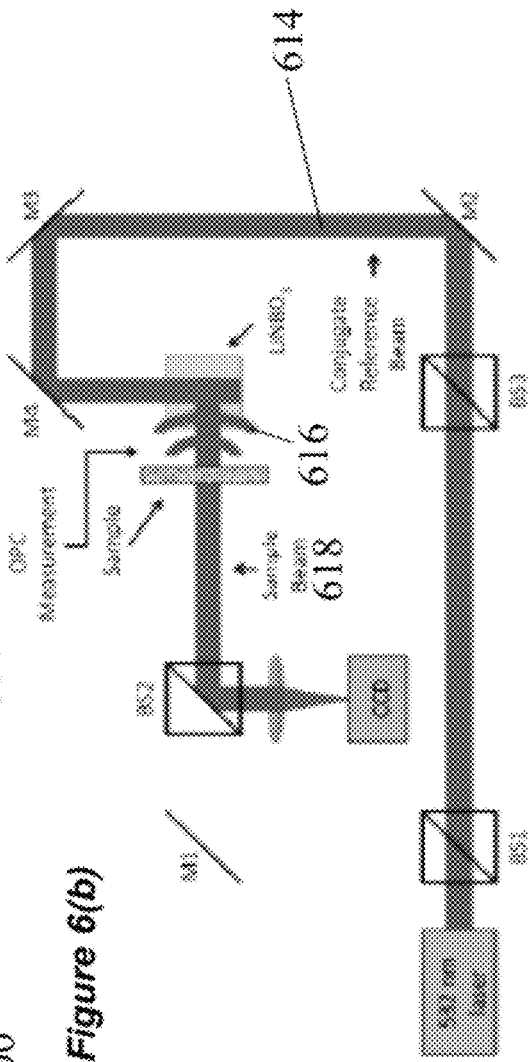
Figure 6(a)
Figure 6(b)
TSOPC setup using LiNBO₃

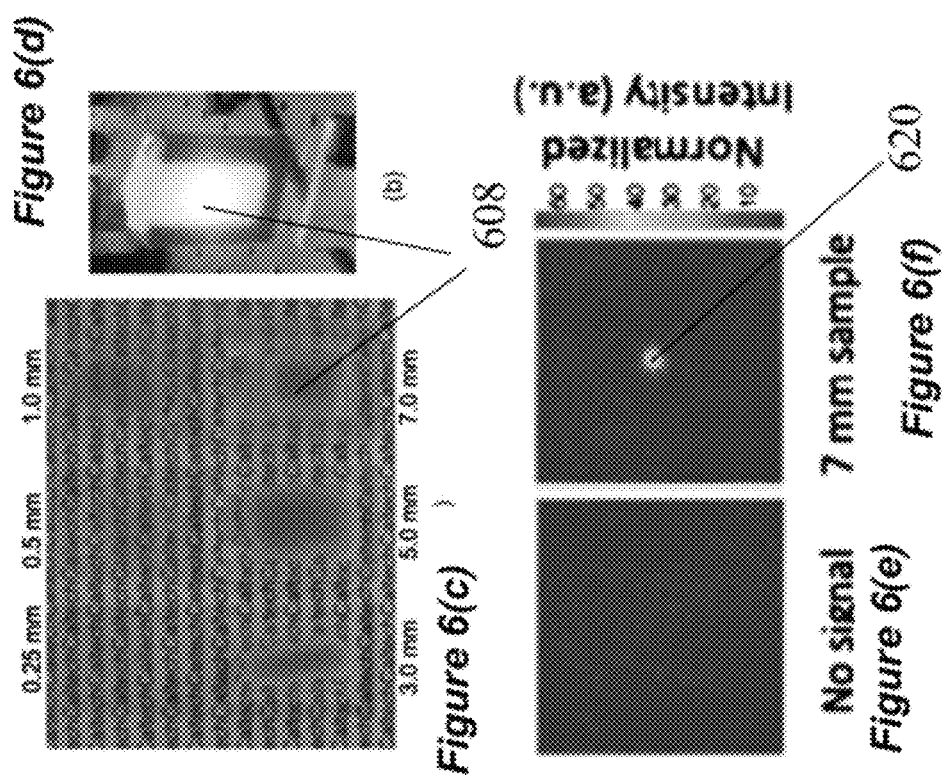

ACOUSTIC-ASSISTED ITERATIVE WAVE FORM OPTIMIZATION FOR DEEP TISSUE FOCUSING

CROSS-REFERENCE TO RELATED APPLICATIONS

This application claims the benefit under 35 U.S.C. Section 119(e) of the following commonly-assigned U.S. provisional patent application(s), which is/are incorporated by reference herein:

Provisional Application Ser. No. 61/384,660, filed on Sep. 20, 2010, by Ying Min Wang and Changhuei Yang, entitled "ACOUSTIC-ASSISTED ITERATIVE WAVE FORM OPTIMIZATION FOR DEEP TISSUE FOCUSING,".

This application is related to the following commonly-assigned patent applications, which applications are incorporated by reference herein:

1. U.S. Utility patent application Ser. No. 12/886,320, filed on Sep. 20, 2010, by Zahid Yaqoob, Emily McDowell and Changhuei Yang, entitled "OPTICAL PHASE PROCESSING IN A SCATTERING MEDIUM," which application is a divisional of U.S. Utility patent application Ser. No. 11/868,394, filed on Oct. 5, 2007, by Zahid Yaqoob, Emily McDowell and Changhuei Yang, entitled "TURBIDITY ELIMINATION USING OPTICAL PHASE CONJUGATION AND ITS APPLICATIONS," which application claims priority under 35 U.S.C. § 119(e) to commonly-assigned U.S. Provisional Patent Application Ser. No. 60/850,356, filed on Oct. 6, 2006, by Zahid Yaqoob, Emily McDowell and Changhuei Yang, entitled "TURBIDITY ELIMINATION USING OPTICAL PHASE CONJUGATION AND ITS APPLICATIONS,";

2. U.S. patent application Ser. No. 12/943,857, filed on Nov. 10, 2010, by Changhuei Yang and Meng Cui, entitled "TURBIDITY SUPPRESSION BY OPTICAL PHASE CONJUGATION USING A SPATIAL LIGHT MODULATOR," which application claims the benefit under 35 U.S.C. § 119(e) of the following commonly-assigned U.S. provisional patent applications, which are incorporated by reference herein:

Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,";

Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION,";

Provisional Patent Application Ser. No. 61/376,202, filed on Aug. 23, 2010, by Meng Cui and Changhuei Yang, entitled "OPTICAL PHASE CONJUGATION 4PI MICROSCOPE,"; and Provisional Application Ser. No. 61/355,328, filed on Jun. 16, 2010 by Meng Cui, Ying Min Wang and Changhuei Yang, entitled "ACOUSTIC ASSISTED PHASE CONJUGATE OPTICAL TOMOGRAPHY,";

3. U.S. Utility application Ser. No. 12/943,841, filed on Nov. 10, 2010, by Meng Cui, Ying Min Wang, Changhuei Yang and Charles DiMarzio, entitled "ACOUSTIC ASSISTED PHASE CONJUGATE OPTICAL TOMOGRAPHY," which application claims priority under 35 U.S.C. § 119(e) to commonly-assigned U.S. Provisional Application Ser. No. 61/355,328, filed on Jun. 16, 2010, by Meng Cui, Ying Min Wang, and Changhuei Yang, entitled "ACOUSTIC ASSISTED PHASE CONJUGATE OPTICAL TOMOGRAPHY,"; U.S. Provisional Application Ser. No. 61/259,975, filed on Nov. 10, 2009, by Changhuei Yang and Meng Cui, entitled "APPROACHES FOR BUILDING COMPACT FLUORESCENCE MICROSCOPES,"; U.S. Provisional Application Ser. No. 61/260,316, filed on Nov. 11, 2009, by Changhuei Yang and Meng Cui, entitled "APPLICATIONS OF TURBIDITY SUPPRESSION BY OPTICAL PHASE CONJUGATION,"; and U.S. Provisional Patent Application Ser. No. 61/376,202, filed on Aug. 23, 2010, by Meng Cui and Changhuei Yang, entitled "OPTICAL PHASE CONJUGATION 4PI MICROSCOPE,"; and U.S. Utility Application Ser. No. 13/157,194, filed on Jun. 9, 2011, by Meng Cui, Ying Min Wang, and Changhuei Yang, entitled "ITERATIVE TIME-REVERSAL ENHANCED TRANSMISSION SOLVING APPROACH," which application claims the benefit under 35 U.S.C. § 119(e) of Provisional Application Ser. No. 61/355,326, filed on Jun. 16, 2010, by Meng Cui, Ying Min Wang, and Changhuei Yang, entitled "ITERATIVE TIME-REVERSAL ENHANCED TRANSMISSION SOLVING APPROACH,";

all of which applications are incorporated by reference herein.

BACKGROUND OF THE INVENTION

1. Field of the Invention

This invention relates to a method and apparatus for reducing diffusion/scattering of light through turbid samples.

2. Description of the Related Art

Optical methods for imaging and targeted medical treatment (e.g. photodynamic therapy (PDT)) are attractive because they are versatile, non-ionizing and relatively cheap (compared to MRI, SPECT, x-ray etc). However, despite the impressive progress in the field of optics, tissue scattering of light presents a major road block in applying these optical methods in deep tissues. Generally, light spreads in tissue, due to diffusion, to an extent that is about several times the thickness of the tissue. As a result, resolution of optical methods rapidly decreases as the thickness of the tissue increases. Also, as light diffuses, the amount of energy is also spread over the area of diffusion. Thus, light with increasingly high energy is required at the entrance side for excitation of fluorophores or PDT agents, for example, in deep tissues. This eventually leads to tissue damage and is therefore impractical and unsafe. In other words, if the tissue scattering problem can be overcome, to deliver focused light to deep tissues, one of the most important barriers in the more widespread utilization of light in biomedical imaging will have been torn down.

Although several methods to overcome the problem of tissue scattering have been proposed, these methods are only able to refocus light through a piece of tissue, but not controllably within the tissue. One of the methods, proposed by Allard Mosk et. al. and illustrated in FIG. 1, uses a spatial light modulator (SLM) to iteratively tailor a wavefront 100 to come to a focus 102 [1]. FIG. 1 illustrates how the initial wavefront 100 of the light 102 incident on an opaque, strongly scattering turbid medium 104 (e.g., $TiO_2$) pigment) is scattered to form diffuse light 106 and does not penetrate deeply into the sample 104. However, like any iterative method, a feedback is required. Mosk's method depends on tracking the fluorescence emitted by a fluorescence bead 106 for feedback control, and using the feedback from the fluorescence bead 108 to tailor the wavefront 100 into a tailored wavefront 110, forming less diffuse light 112, thereby focusing and penetrating the light 112 more deeply into the sample 104. (FIG. 1 is based on the cartoon depiction on page 1107 of the publication entitled "the most transparent research," Nature medicine, Volume 15, Number 10, October 2008).

It is apparent that this method has yet to address several impediments that prevent its direct application to biomedical applications. Firstly, this method will not work if there is a fairly homogenous distribution of fluorophores 104 throughout the sample, since it is then impossible to select the fluorophore 104 to focus to. Secondly, it is impossible to determine the location of the fluorophore even if focusing is achieved (assuming that it is unlikely that the biological tissue has fluorophores concentrated, rather than diffused, in a small area). In other words, this method will only work on specific samples with a concentrated area of fluorophores and a pre-knowledge of the fluorophore location.

One or more embodiments of the present invention detail an idea that combines acousto-optic interaction with the wavefront optimization described by Mosk's group [1] to achieve light focusing in deep tissues, thus finally overcoming an important problem in biomedical optics.

SUMMARY OF THE INVENTION

One or more embodiments of the present invention disclose a method for irradiating a target within a sample, comprising (a) controllably defining a target within a sample with an acoustic field; (b) irradiating the sample with input Electromagnetic (EM) radiation having an input wavefront; (c) detecting an amount of frequency shifted EM radiation, wherein at least some of the input EM radiation that passes through the acoustic field at the target is shifted in frequency by the acoustic field to form the frequency shifted EM radiation; (d) modifying the input wavefront, using feedback comprising the amount of the frequency shifted EM radiation that is detected, into a modified wavefront; and (e) repeating the irradiating step (b) using the modified wavefront as the input wavefront.

The method can further comprise repeating steps (a)-(e) until a threshold intensity or desired focus of the input EM radiation at the target is achieved, wherein the modifying comprises selecting the modified wavefront that maintains, increases, or maximizes the amount of the frequency shifted EM radiation as compared to the amount of the frequency shifted EM radiation obtained using the input wavefront.

The acoustic field can be focused to produce a first focus of the acoustic field at the target, and the modified wavefront converges to form a second focus of the input EM radiation at the target.

The acoustic field can comprise ultrasound. For example, the ultrasound can be focused to an ultrasound focal spot at, or defining the target, the ultrasound focal spot can have a diameter of 100 micrometers or less at a depth of at least 5 mm within the tissue, and the input EM radiation can be focused to at most a same size as the ultrasound focal spot or target.

The modified EM radiation can be used as the EM radiation source in one or more applications.

In one application, the input EM radiation comprising the modified wavefront can be used to perform Raman spectroscopy of the target.

In another application, the irradiating of the sample can include selecting a frequency of the EM radiation that enables multi-photon excitation of the targets.

In biomedical applications, the sample can comprise biological tissue, wherein the input EM radiation does not damage, affect, or adversely affect tissue that is not at one of the targets. The input EM radiation comprising the modified wavefront can be used to cut the tissue at, and defined by, the target, wherein the target is at a depth of at least (but not limited to) 5 mm from a surface of the tissue.

The method can further comprise performing photodynamic therapy on the tissue, wherein the input EM radiation having the modified wavefront excites a photosensitive agent at the target to trigger the photodynamic therapy of the tissue at the target.

One or more embodiments of the present invention disclose an apparatus for performing one or more embodiments of the method. The apparatus can comprise means for generating and transmitting an field (e.g., acoustic field) that controllably defines one or more targets within the sample (e.g., an acoustic wave source and control system); (b) means for irradiating the sample with input EM radiation having an input wavefront (e.g., an EM radiation source, such as a laser, light emitting device, and a control system, such as an imaging/focusing lens system); (c) a detection system or means, for detecting (and also, optionally, quantifying) an amount of the frequency shifted EM radiation, wherein at least some of the input EM radiation that passes through the acoustic field at the target is shifted in frequency by the acoustic field to form frequency shifted EM radiation; and (d) means for modifying or tailoring the input wavefront (e.g., a wavefront modifying or tailoring device, such as an SLM or DMD), using feedback comprising the amount of the frequency shifted EM radiation that is detected in the detection system, into a second wavefront; and wherein the modified wavefront is used as the input wavefront.

BRIEF DESCRIPTION OF THE DRAWINGS

Referring now to the drawings in which like reference numbers represent corresponding parts throughout:

FIG. 6(a) and FIG. 6(b) illustrate a set up for generating phase conjugate light to illuminate and transmit through tissue samples;

FIG. 6(c) illustrates chicken breast tissues of varying thickness;

FIG. 6(d) illustrates one of the chicken breast samples of FIG. 6(c) mounted in the setup of FIGS. 6(a) and 6(b);

FIG. 6(e) illustrates that no signal is measured on a CCD placed on the exit side of the 7 mm thick sample 608 of FIG. 6(c);

FIG. 6(f) illustrates that a strong focused signal (focal spot 620) is measured on a CCD when the 7 mm thick sample 608 of FIG. 6(c) is illuminated with the phase conjugate sample beam; and FIGS. 7(a)-(b) illustrate that an SLM can be used to produce the phase conjugate sample beam, wherein FIG. 7(a) shows a phase map of the speckle pattern produced when a flat wavefront is sent through a scattering medium comprising paint, and FIG. 7(b) shows that well aligned Digital Optical Phase Conjugation device (DOPC) sends back a phase conjugate wavefront that results in a focused spot (the image is displayed on logarithmic scale).

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

In the proposed method of one or more embodiments of the present invention, a high frequency ultrasound transducer is used to define an ultrasound focus within a tissue. Light that passes through the ultrasound focus is frequency-shifted. Several methods, including digital holography [2] and confocal fabry perot interferometer [3], can be used to detect the frequency-shifted light. By detecting the amount of frequency-shifted light as a feedback, the input wavefront is iteratively tailored using a SLM or a deformable mirror device, such that the resulting wavefront comes to a tight focus at the ultrasound focus. In other words, this iterative method results in a wavefront that focuses at any location, defined by the ultrasound focus, in the deep tissue. This focused light spot can find wide usage in biomedical applications, for example in imaging, Raman spectroscopy for chemical detection, and as a deep tissue scalpel, etc.

Technical Description

Unlike light, ultrasound is very weakly scattered in tissues. Thus, it is possible to form an ultrasound focus spot in tissue. As light interacts with ultrasound, it gets shifted in frequency, typically as a result of a photon-phonon interaction. The frequency shift means that light that passes through an ultrasound focus becomes tagged. Making use of this tagging, one or more embodiments of the present invention can selectively detect and quantify the amount of light that has passed through an ultrasound focus.

Tailoring a wavefront for focusing light through a piece of turbid media 104 is an idea first proven by Allard Mosk's group at Universiteit van Amsterdam [1]. The basic idea is that the input wavefront can be spatially modified using a spatial light modulator (SLM), or a deformable mirror device (DMD), and tailored before passing into a tissue such that the light may converge and combine constructively within the tissue. However, as mentioned above, currently emitted fluorescence from an excited fluorophore (at a known location with no other fluorophore in its vicinity) is used for feedback in this process. This is an impractical geometry/requirement for biomedical applications.

Figure 1:
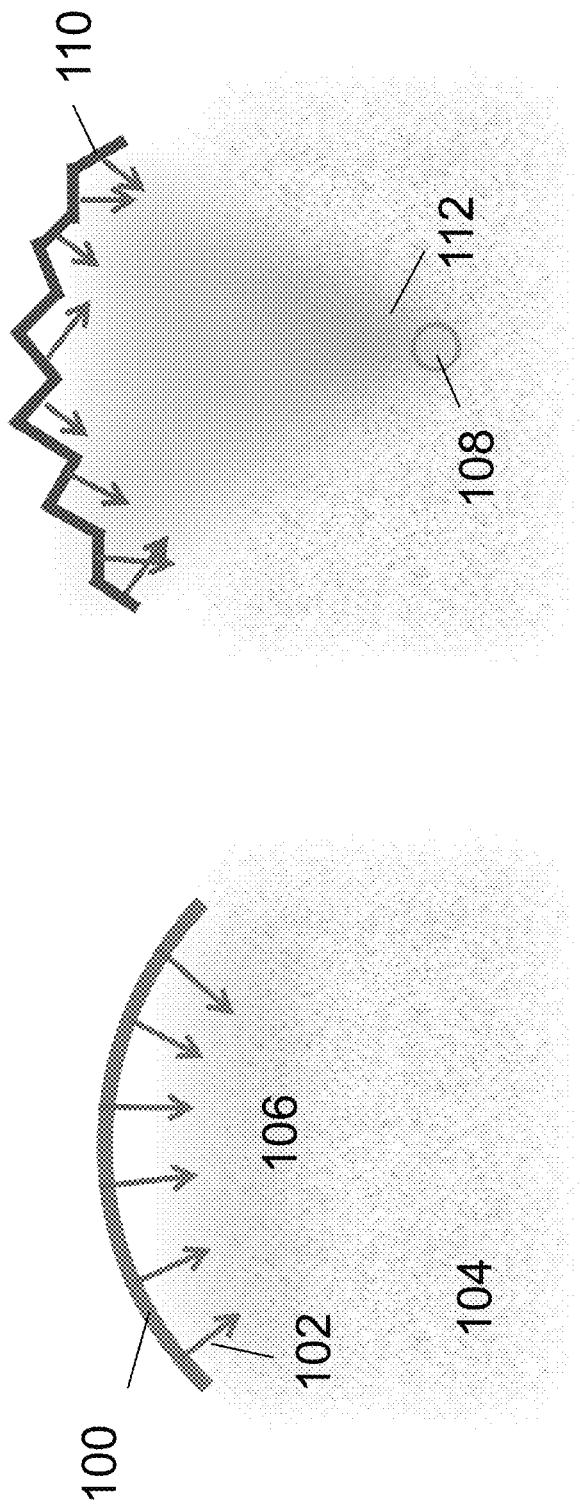
FIG. 1 is a schematic of Mosk's wavefront optimization scheme, wherein a uniform wavefront is scattered as it passes through a turbid sample, and using optimization, a tailored wavefront can focus to a spot [1] (FIG. 1 is based on the cartoon depiction on page 1107 of the publication entitled "the most transparent research," Nature medicine, Volume 15, Number 10, October 2008)
Figure 2A:
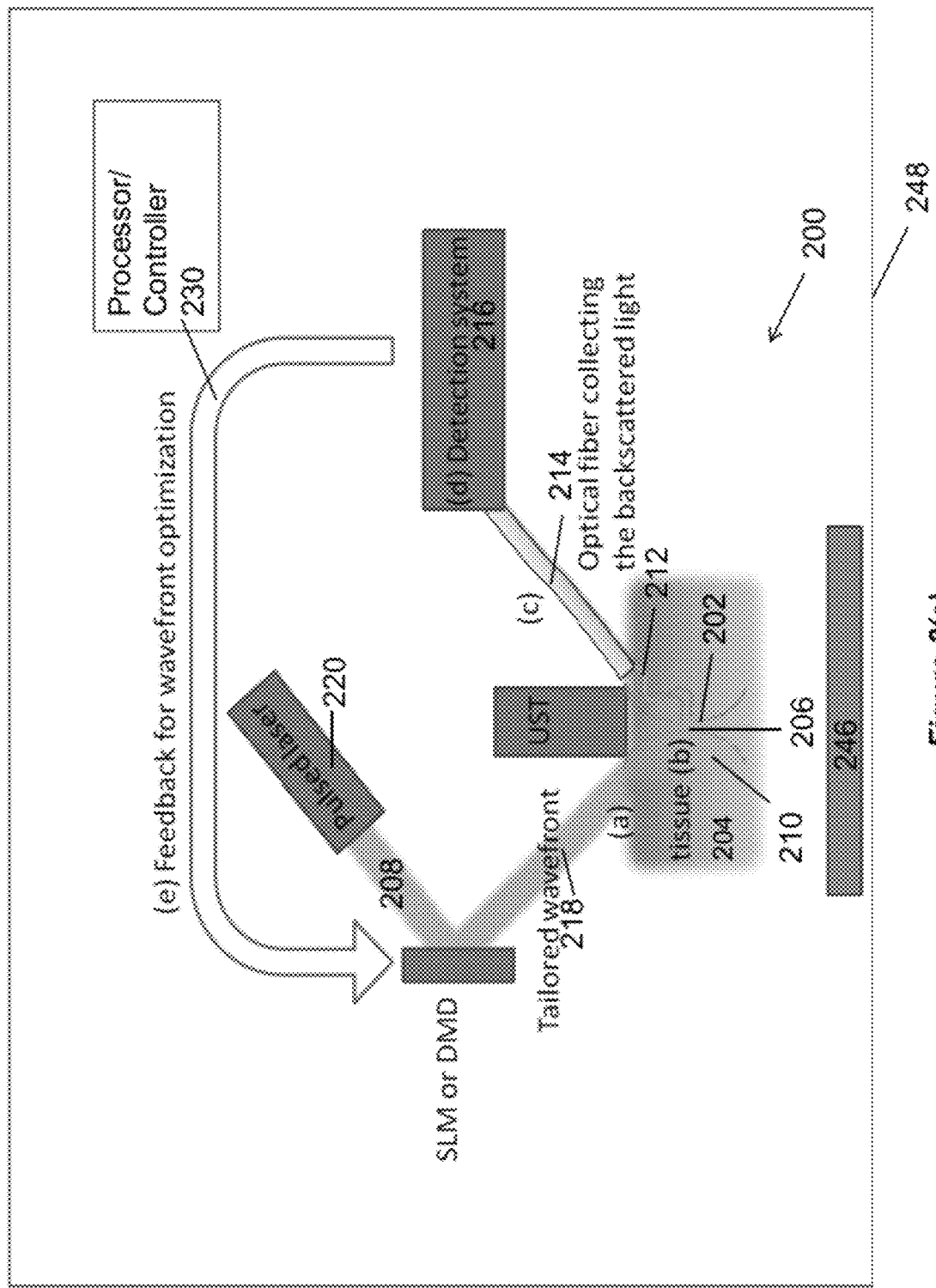
FIG. 2(a) illustrates a schematic of the principle of operation of one or more embodiments of the present invention.

FIG. 2(a) illustrates an acoustic-assisted iterative waveform optimizer 200 and method of operation, according to one or more embodiments of the present invention, wherein the two principles mentioned above are combined. First, an ultrasound beam 202 from an ultrasound transducer (UST) is focused in the tissue 204 so that an ultrasound focus 206 in the tissue 204 is defined. As shown in (a), light 208 incident on the tissue 204, entering the tissue 204, and travelling through the tissue 204 is highly scattered to form scattered light 210. As shown in (b), some of the light 208 (or part of the scattered light 210) passes through the ultrasound focus 206 generated by the UST and is frequency-shifted (e.g., up-shifted in frequency) to form frequency-shifted light 212. As shown in (c), an optic fiber 214 (for example) collects the backscattered 212 or frequency-shifted light 212, some of which has passed through the ultrasound focus 206, and the fiber 214 guides the frequency-shifted light 212 for detection in a detection system 216. As shown in (d), the detection system 216, which can comprise of an interferometry setup or a confocal fabry perot interferometer, can be used to detect and quantify the frequency-shifted light 212 collected by the fiber 214. Alternatively, the detection system 216 can detect the light frequency-shifted light 212 by methods such as digital holography or locked-in detection (if the ultrasound pulses are also amplitude modulated at a significantly lower carrier frequency). As shown in (e), the amount of frequency shifted light 212 that is detected in (d) is used as a metric for feedback for wavefront optimization by the SLM or DMD to form a tailored wavefront 218, such that light is focused at the ultrasound focus spot 206. For example, the input wavefront of the light 208 incident on the tissue 204 in (a) is tailored by a SLM or DMD into the tailored wavefront 218, while receiving feedback via monitoring the amount of frequency-shifted light 214, such that eventually most light 208 passes through and constructively interferes at the ultrasound focus 206 (and is thus frequency-shifted into frequency shifted light 214), effectively forming an optical focus at the location defined by the ultrasound focus 206.

The x and y resolution of this method are limited by the size of the ultrasound focus 206, which is in turn affected by the ultrasound 202 frequency and numerical aperture of the acoustic lens used to focus ultrasound 202 waves at the focus 206. The z resolution of the ultrasound focus 206 can be minimized by pulsing the ultrasound 202 from the UST and the source of the light 220 (e.g., a pulsed laser 220), such that the laser's 218 light 208 and the ultrasound 202 only interact at a specified z location.

Figure 2B:
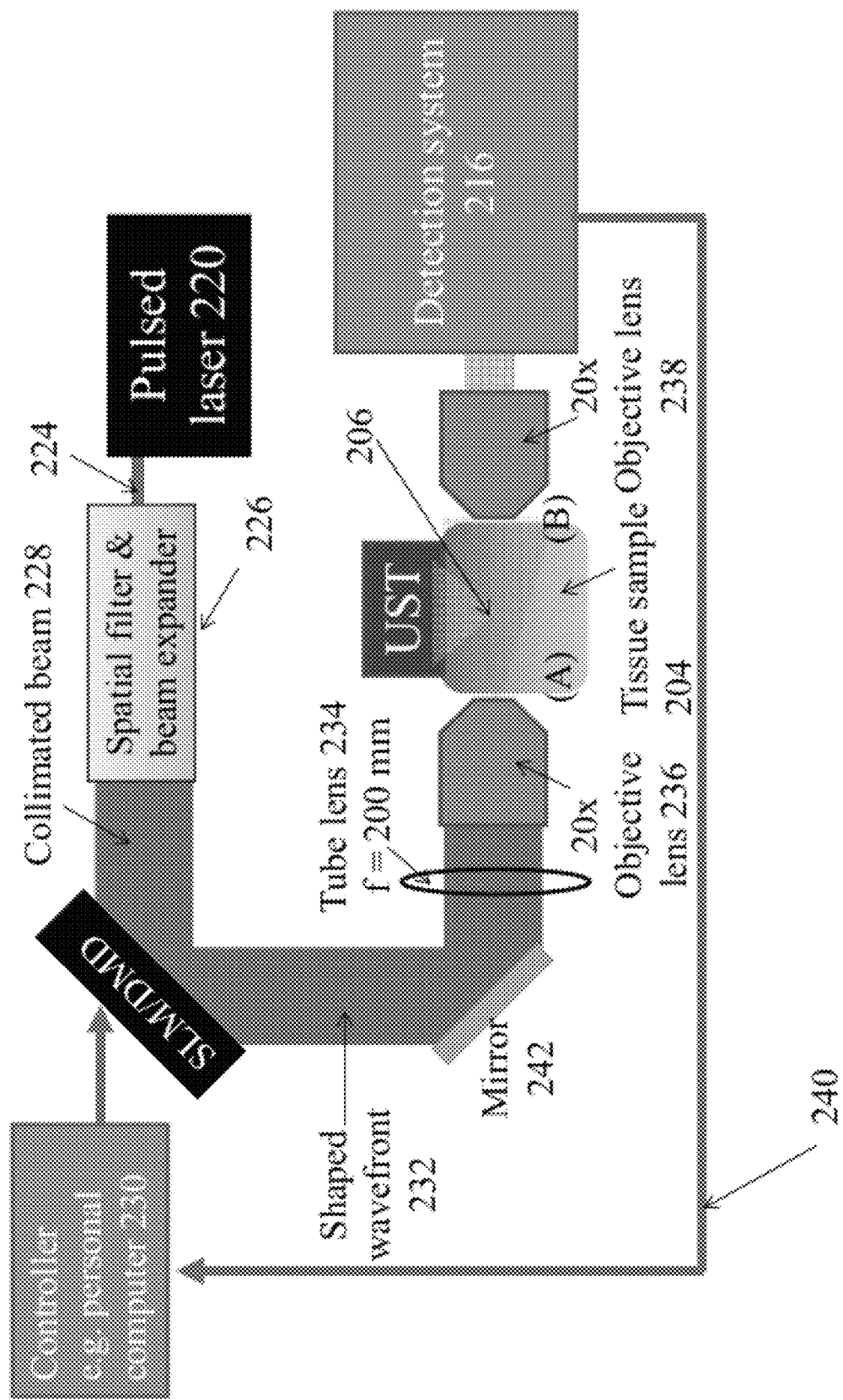
FIG. 2(b) illustrates the optics that could be used in the wavefront optimization method, according to one or more embodiments of the present invention.

FIG. 2(b) illustrates an example of the optics that could be used in one or more embodiments of the wavefront optimization method of the present invention. The output light or beam 224 of the pulsed laser 220 is spatial filtered and expanded in a spatial filter and beam expander 226. The expanded, collimated beam 228 reflects off a wavefront shaping device (for example, SLM or a Deformable mirror array device (DMD)) controlled by, for example, a controller 230 such as a personal computer. The reflected wavefront is thus shaped into a shaped wavefront 232 and is relayed to the tissue sample 204 by, for example, a tube lens 234 (e.g., focal length f=200 mm) and a 20× objective lens 236. The light input on side (A) is scattered and some of the scattered light enters the ultrasound focus 206 produced by a focused ultrasound transducer (UST) and is thus frequency-shifted. The output scattered light at side (B) can be collected by a 20× objective lens 238. The amount of frequency-shifted light collected can be measured by the detection system 206, which feedbacks 240 to the controller 230. Also shown in a mirror 242 for directing/reflecting the collimated beam 228 with shaped wavefront 232 onto the tissue 204.

Figure 2C:
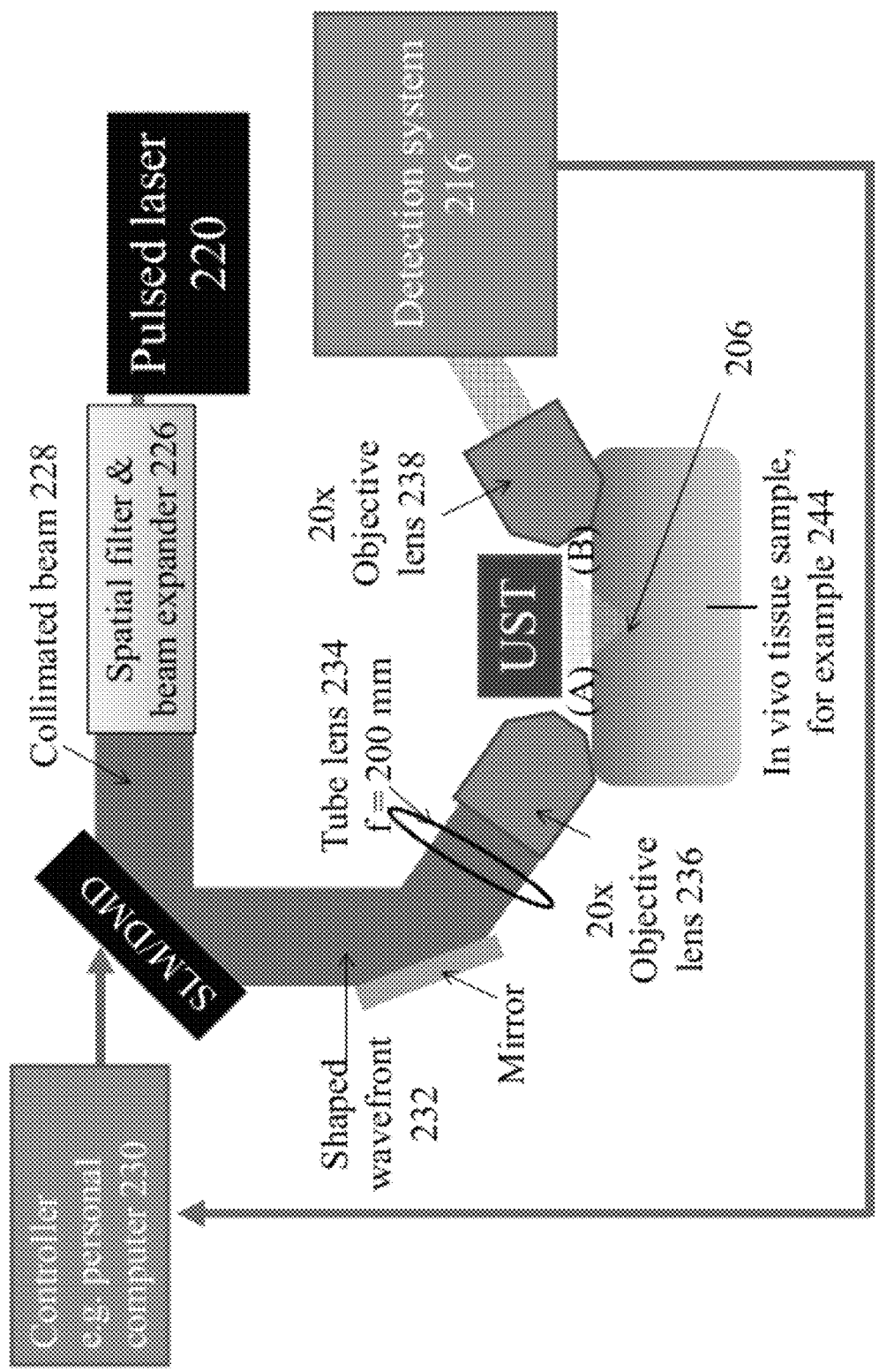
FIG. 2(c) illustrates another configuration for the light input optics and collection optics, according to one or more embodiments of the present invention.

The light input (side A) and collection (side B) can also be in the configuration where the light input optics (e.g., SLM, lens 234, objective 236) and collection optics (e.g. 238) are on the same side as the ultrasound transducer UST so it is possible for use in whole tissues or in vivo samples 244, as shown in the embodiment illustrated in FIG. 2(c).

The SLM (or the wavefront shaping device) and a computer 230 can control the phase and/or amplitude of input electromagnetic (EM) radiation 208 incident on the SLM via, but not limited to, one of the following algorithms:

1. The phase and or amplitude of the input EM radiation 208 incident on the SLM can be varied pixel by pixel such that the input EM radiation 208 reflected from the pixels of the SLM is incident on the sample and has a controlled phase [4].
2. This method can be sped up by using simultaneously modulating pixels on the SLM, each at a unique frequency according to the procedures in reference [5]. The detected levels of ultrasound frequency-shifted EM-radiation over time would thus fluctuate with the frequencies of the pixels' modulation frequencies. If the frequency-shifted EM-radiation signal is Fourier transformed, the phase values of the encoded frequency corresponding to each pixel on the SLM can be derived.
3. A third example of modulating the shape of the input waveform is by controlling the SLM such that it modifies the input wavefront at each step using the Hadamard basis (Walsh matrix) [6, 7].

While one or more embodiments of the present invention can perform waveform modification/optimization using one or more of the published procedures [4-8], the present invention is not limited to these procedures. Other procedures for wavefront modification/optimization can also be used.

At each step of one of wavefront modulations using one of the above wavefront modulation methods, the amount of corresponding frequency-shifted EM radiation at the output face is measured. As compared to the non-frequency shifted EM radiation, the amount of frequency-shifted EM radiation can be on the order of $10^{-4}$ or less. Furthermore, the frequency shifted EM radiation is not spatially distinct from the non-frequency shifted light. To measure such a small signal on top of a large background, one of the following examples of frequency-shifted EM radiation detection methods can be used:

1. By interfering the output EM field (e.g., collected EM radiation exiting the sample and collected by objective 238) with a tilted reference beam at the same frequency as the frequency-shifted EM radiation (this can be achieved by shifting the EM field by an acousto-optic modulator for example), the interference pattern made by the frequency-shifted light can be confined to a distinct region in k-space (spatial frequency space). Using digital phase-shifting holography [9], the amount of power in that particular region in the k-space can be determined, thus determining the amount of frequency-shifted EM radiation collected [10].
2. The frequency-shifted radiation can also be picked out from the large background by the use of a photorefractive crystal. A hologram is recorded by interfering the output EM radiation (frequency-shifted and non-shifted) with a reference beam (frequency-shifted) in a photorefractive crystal. This reference beam also acts as a readout beam for the hologram. As the phase of ultrasound wave is oscillated (from 0 to π), the frequency-shifted radiation interferes constructively and destructively (respectively) with the hologram played back by the readout beam. This oscillating signal can be recorded on a large area photodiode and the amplitude of that signal corresponds to the amount of frequency-shifted light collected at the output face [11].
3. In another example, frequency-shifted EM radiation can be distinguished from non-shifted EM radiation and measured with the use of a confocal Fabry-Perot interferometer (CFPI). By tuning the resonant frequency of the CFPI cavity to the ultrasound-modulated EM radiation frequency, the signal output from the CFPI (measured by a Avalanche Photodiode, for example) corresponds to the amount of frequency-shifted EM radiation [12].

While one or more embodiments of the present invention can detect frequency shifted light using the published procedures [9-12], the present invention is not limited to these procedures. Other procedures can also be used for detection of frequency shifted light.

Iteration algorithms can also be used to speed up the iterative process illustrated in FIG. 2. In addition, the iterative process can be completed in shorter times by using more advanced computer software and hardware technologies, in a processor 220 that decreases computation time. Furthermore, using a DMD instead of a SLM can speed up the process of FIG. 2 by orders of magnitude, because of the DMD's faster refresh rate. Although the DMD provides only amplitude modulation, it is theoretically and practically possible to iteratively construct the optical focus with just amplitude modulation. The scheme of FIG. 2 can be performed with optical fibers 214 with no demanding alignment, thus making the geometry very favorable for biomedical applications.

Process Steps

Figure 3:
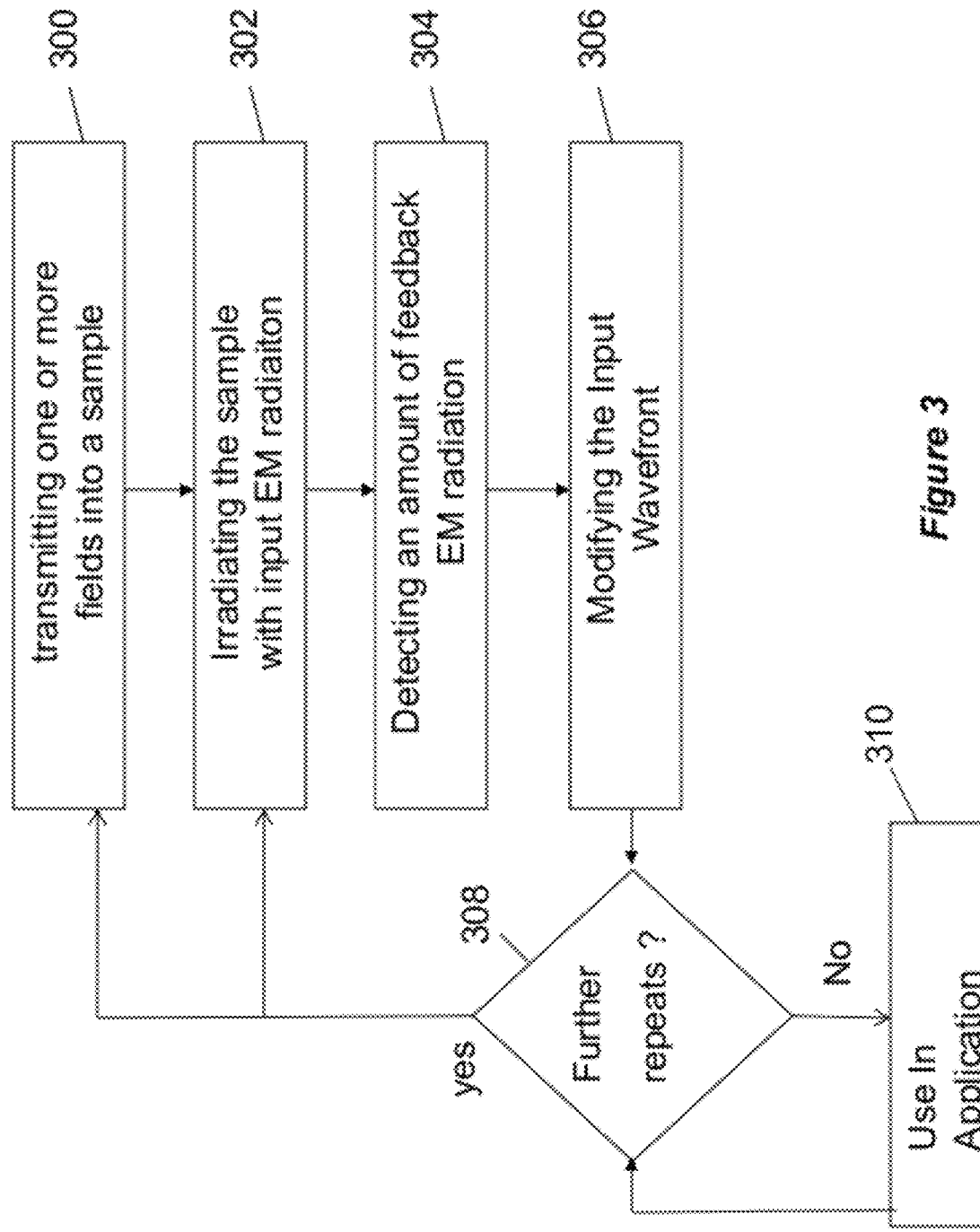
FIG. 3 illustrates a method of irradiating a target within a sample with electromagnetic (EM) radiation, according to one or more embodiments of the present invention.

FIG. 3 illustrates a method for irradiating one or more targets within a sample with electromagnetic (EM) radiation, according to one or more embodiments of the present invention. The sample can be a turbid, strongly scattering medium, or biological tissue (e.g., a tissue section, part of a human, animal, or plant body, including bone, in vivo or removed from the body).

Block 300 represents transmitting one or more fields into a sample to define one or more targets within the sample. For example, the step can comprise controllably defining one or more targets with the one or more fields (e.g., varying/selecting a size, area, volume, and shape of the targets using the one or more fields).

The one or more targets can comprise one or more target areas or volumes in/of the sample that are included within, bounded by, defined by the fields' beam shape, waist, or focus. The fields can be focused only at the targets, resolve the targets, distinguish the targets from a background of the sample (where illumination or irradiation is not desired), or define a target area that includes a portion of the tissue/sample to be treated/reduced/destroyed/excited by the input EM radiation.

The target area or volume can include/surround/locate/bound/define selected constituent parts of the sample. For example, in the case of the sample that is tissue, the target area or volume can include selected cells, lesions, cancerous tumors, or foreign bodies implanted in the tissue (such as nanoshells, absorbing dye molecules, or light activated molecules). The target can comprise one or more photosensitive agents placed in the tumor, wherein the photosensitive agents trigger photodynamic therapy of the tumor.

The fields can comprise one or more acoustic fields or waves, such as ultrasound, or EM fields having a longer wavelength (e.g., infrared, far-infrared, terahertz, or radio waves) that are less scattered by the sample than optical or visible EM wavelengths.

The transmitting 300 can comprise propagating the fields from one or more sources of fields external to the sample. The transmitting 300 can comprise transmitting one or more signals into the sample to define the one or more targets within the sample Block 302 represents irradiating/illuminating the sample with first (or input) EM radiation having one or more first (or input) wavefronts.

The input EM radiation can comprise light, e.g., having optical, visible, or near infrared wavelengths, 0.3 micrometers to 10 micrometers wavelength, for example. The input EM radiation can be coherent radiation or light (e.g., from a laser). The input EM radiation can be pulsed in synchronism with the fields of Block 300.

The irradiating 302 can include selecting a frequency of the input EM radiation that enables multi-photon excitation of the targets defined in Block 300. One or more embodiments of the present invention enable the use of a sample that does not contain fluorophores, and/or use a wavelength of the input EM radiation that is longer than is typically used to excite a fluorophore in tissue (e.g., but not limited to, a wavelength range from >300 nm to 1 micron, and the wavelength range for multi-photon excitation).

Block 304 represents detecting (e.g., quantifying) an amount (e.g., intensity) of second (or feedback) EM radiation, wherein at least some of/a portion of/all of the input EM radiation (irradiating 302 the sample) that passes through the fields at the targets (defined in Block 300) interacts with the fields to form the feedback EM radiation. The input EM radiation can be modulated by the signal(s) (produced in Block 300) into modulated EM radiation as the input EM radiation passes through the targets concurrently with the signals, wherein the modulated EM radiation is used as the feedback EM radiation. The feedback EM radiation can comprise frequency shifted EM radiation, wherein at least some of the input EM radiation that passes through the acoustic field (e.g., ultrasound) produced in Block 300 at the target is shifted in frequency by the acoustic field to form the frequency shifted EM radiation.

The feedback EM radiation can be detected in a detection system by a holographic, interferometric, or lock in method, for example.

Block 306 represents modifying the input wavefront(s), using feedback comprising/in response to the amount/intensity of the feedback EM radiation that is detected in step 304, into one or more modified wavefronts.

The input wavefronts can be modified 306 to increase the intensity of feedback EM radiation that is detected. For example, the modifying 306 can comprise selecting the modified wavefront that maintains, increases, or maximizes the amount of the frequency shifted EM radiation as compared to the amount of the frequency shifted EM radiation obtained using the input wavefront before modification.

The modifying 306 can use an SLM or DMD, or other digital methods, for example. For example, EM radiation can be reflected off one or more pixels of the SLM or DMD to form the input EM radiation irradiating 302 the sample, and the modifying 306 can comprise controlling the pixels to produce the phase or shape of the wavefront of the input EM radiation that increases the amount of the feedback EM radiation that is detected (as compared to before the modification). The modifying 306 can comprise raster scanning the position of the SLM pixels so that the phase of the input EM radiation is cycled from 0 to $2\pi$, detecting 304 the amount of the feedback EM radiation for each phase data point, and selecting the position of the SLM pixels that maximizes the amount of feedback EM radiation.

This modification results in increased intensity, or more focused input EM radiation at the target. The modifying 306 can comprise modifying a phase of one or more electric fields of the input EM radiation (e.g., using the SLM or DMD) such that constructive interference of one or more of the electric fields occurs at the target to form the increased intensity of the input EM radiation. The modifying 306 can also comprise modifying an amplitude of the one or more electric fields of the input EM radiation to increase the intensity of the input EM radiation transmitted to the target.

Block 308 represents at least repeating the irradiating step 302 using the one or more modified wavefronts produced in Block 306 as the one or more input wavefronts in the subsequent irradiating step 302.

The modified wavefront can comprise a non-diffusing wavefront, inverse diffusing wavefront, a converging, focused, or collimated EM radiation, that is more focused, less scattered, or less diffused by the sample as compared to the input wavefront.

If the acoustic field in Block 300 is focused to produce a first focus of the acoustic field at the target, the modified wavefront may converge to form a second focus of the input EM radiation at the target, wherein the second focus overlaps with the first focus (or does not extend over an area larger than the target). If one or more acoustic fields are focused to produce an acoustic field focus at each of multiple targets, increased intensity may be at a plurality of foci of the input EM radiation, located at each of the multiple targets. For example, the acoustic field can comprise ultrasound that is focused to an ultrasound focal spot at the target, the ultrasound focal spot can have a diameter of 100 micrometers or less at a depth of (but not limited to) at least 5 millimeters within the tissue, and the input EM radiation can be focused to at most a same size as the ultrasound focal spot, or to within a single speckle grain, for example.

The repeating 308 can further repeat the defining 300, detecting 304 and modifying 306 steps (e.g., two or three or more times) until a threshold intensity or desired focus of the input EM radiation at the target is achieved. For example, the step can comprise repeating (e.g., iteratively) steps 300-306 to form a number of incidences of the input EM radiation onto the sample, wherein each incidence results in a modification of the input wavefront, and the modified input wavefront is used as the input wavefront in a next incidence of the input EM radiation. In this way, the number of incidences may be increased and selected to obtain the desired input EM radiation at the targets (e.g., desired intensity or focal size of the input EM radiation at the targets).

For example, The steps 300-306 can be repeated to increase the intensity of the input EM radiation at the targets, e.g., until a maximum intensity at, a threshold or minimum focus size of the input EM radiation, a threshold or maximum transmittance of the input EM radiation to, the one or more targets is achieved.

The steps 300-306 can be repeated to produce the modified wavefront corresponding to a phase conjugate of the input wavefront. The modifying 306 can phase conjugate the input EM radiation or fields to form phase conjugate EM radiation or fields, wherein the phase conjugate EM radiation is used as the input EM radiation in a next incidence or irradiation 302.

The transmitting 300 of one or more fields into the sample can be repeated/maintained as necessary to define the one or more targets at least for the interaction of the input EM radiation with the fields and detection of the feedback EM radiation.

The repeating 308 can further comprise determining whether further repeats of 300-306 are necessary. If yes, the iterative or repeating procedure may be continued. If not, the input EM radiation comprising the modified wavefront may be used in an application.

The input EM radiation prior to modification 396 can be plane wave, spherical wave, or any arbitrary shaped beam of light, including collimated beams of light, etc. Therefore, the input EM radiation is not limited to a particular beam shape—a wide range of beam shapes can be used. In some embodiments, the "shape" of the input EM radiation beam after modification 306 is equivalent to the phase conjugate of the scattered wave.

While lensing systems can be used in one or more embodiments, no particular lensing systems are required (general lensing systems can be used). In one or more embodiments, some typical configurations to image the SLM pixels onto the entrance of an objective lens can be used.

Block 310 represents using the input EM radiation comprising the modified wavefront for various applications.

One or more embodiments perform acoustic-assisted iterative wave form optimization for deep tissue focusing or imaging (e.g., in a medical surgical or imaging device). The modified wavefront can be an optimized wavefront for obtaining a focus of the input EM radiation at the target.

For example, the input EM radiation comprising the tailored or modified wavefront can perform deep tissue incisions or surgery without cutting through or damaging superficial or portions of the tissue that should not be cut or damaged (e.g., the input EM radiation does not damage tissue that is not at one of the targets). For example, the input EM radiation comprising the modified wavefront can be used to cut the tissue located at/defined by the target, wherein the target is at a depth of at least 5 mm from a surface of the tissue.

In other examples, the input EM radiation can perform photodynamic therapy. In photodynamic therapy, the input EM radiation having the modified wavefront can excite one or more photosensitive agents attached to a cancer drug at the target (or placed at multiple targets) in the tissue, wherein the input EM radiation activates the cancer drug that destroys or reduces the size of the cancerous tumors located at the target(s). In this way, the input EM radiation having the modified wavefront(s) triggers the photodynamic therapy of targets or tissue at the targets.

In yet other examples, the input EM radiation comprising the modified wavefront can be used to perform Raman spectroscopy of the target.

Further repeats 308 of steps 300-306 can be performed during the application, thereby continuously re-optimizing and compensating for scatterers in the sample shifting over time. For example, repeating 308 steps 300-306 may update/ increase the number of incidences to maintain the focus or increase the intensity of the input EM radiation at the target(s) as a function of time. In one or more embodiments, the number of incidences depends on feedback from a result of the application step 310. Therefore, the repeating 308 and determining whether further repeats are necessary can be performed before, during, or after the application step 310.

Measurements have found that tissue movements can cause scatterer position shifts. However, the steps 300-308 could be performed the time over which tissue and scatterers within tissue are stable or do not move appreciably to effect the iteration. One or more embodiments perform the iteration, or select the number of repeats of 300-308 so that the procedure is faster than a few seconds (or faster than the time for scatterer position shifts).

Accordingly, one or more embodiments of the present invention disclose a method for irradiating a sample with input EM radiation, comprising tracking an amount/magnitude of an interaction between the input EM radiation and an acoustic wave or field, and forming a tailored or optimized wavefront of the input EM radiation with reduced scattering using feedback from the tracked interaction. The tailored wavefront may enable an increased intensity or focusing of the input EM radiation at the target. The fields of Block 300 are typically selected so they are scattered less than the input EM radiation (e.g., selecting fields that are acoustic fields or EM fields having wavelengths longer than the input EM radiation).

Steps can be added or omitted, as desired.

Apparatus

The above method can be performed/implemented using the apparatus described in FIG. 2. FIG. 2 illustrates an apparatus 200 for irradiating a target within a sample, comprising (a) an acoustic wave source (e.g., UST) and control (e.g., imaging/focusing) system for transmitting an acoustic field that controllably defines one or more targets within the sample 204 with the one or more acoustic waves 202; (b) an EM radiation source 220 and control (e.g., imaging/focusing) system for irradiating the sample 204 with input EM radiation 208 having an input wavefront; (c) a detection system 216 for detecting (and also, optionally, quantifying) an amount of the frequency shifted EM radiation 212, wherein at least some of the input EM radiation 208 that passes through the acoustic field 206 at the target is shifted in frequency by the acoustic field to form frequency shifted EM radiation 212; and (d) a wavefront modifying or tailoring device (SLM or DMD) for modifying or tailoring the input wavefront, using feedback comprising the amount of the frequency shifted EM radiation 212 that is detected in the detection system 216, into a second wavefront 218; and wherein the modified wavefront is used as the input wavefront. The acoustic wave source and control system can focus ultrasound focal spots having a diameter of 100 micrometers or less, for example.

One of ordinary skill in the art understands that a number of elements of the invention can be mixed and matched to obtain a variety of embodiments.

An example of the UST includes, but is not limited to, a focused ultrasound V3320, Olympus NDT [13]. An example of a function generator for driving the UST includes, but is not limited to, a Tektronix AFG3102, whose signal, in one or more embodiments, may be amplified by a radio frequency (RF) amplifier (e.g., 30W1000B, however other amplifiers or, no amplifiers, can be used). The ultrasound transducer can be coupled to the sample 204 with ultrasound transmission gel or by immersing the sample 204 and the transducer element in a water bath, for example.

In one or more embodiments, the following parameters/ configuration can be used. A 50 MHz, 20 ns pulse is generated by a function generator. The repetition rate of this pulse is 20 kHz (matching the repetition rate of the pulsed laser 220, also operating at 20 kHz). This signal is amplified by a RF amplifier to reach 50 Vpp at the input to the ultrasound transducer. This value can be lower (producing less frequency-shifted EM radiation) or higher (producing more frequency-shifted EM radiation) depending on the characteristics of the tissues and the sensitivity of the frequency-shifted EM radiation detection system 216. The maximum signal input to the ultrasound transducer depends on the transducer specifications (a typical average maximum input power=0.125 W). However, this configuration/these parameters are merely provided as examples, and other configurations/parameters are possible. Further information on photon interaction with ultrasound can be found in [14]. Acoustic assisted phase conjugate optical tomography is also discussed in U.S. Utility application Ser. No. 12/943,841, filed on Nov. 10, 2010, by Meng Cui, Ying Min Wang, Changhuei Yang and Charles DiMarzio, entitled "ACOUSTIC ASSISTED PHASE CONJUGATE OPTICAL TOMOGRAPHY," which application is incorporated by reference herein.

An example of the EM radiation source 220 includes, but is not limited to, a Spectra Physics Navigator 532-3 laser [15].

One or more embodiments of the present invention are not limited in the optics used to image/focus the input EM radiation onto the sample and the SLM. The optics can be generic. For example, the input EM radiation can use a lens pair to collimate and expand the laser beam onto the SLM, and the EM radiation from the SLM can be imaged onto the sample using an objective with an appropriate numerical aperture. One example of a lens configuration is a 20× microscope objective 236 (e.g., CFI Plan APO VC 20×NA 0.75 WD 1 mm) and a tube lens 234 (f=200 mm) that images the SLM's pixels to the back aperture of the microscope objective 236.

The SLM can comprise, but is not limited to, a Holoeye PLUTO-VIS. 1920×1080 pixels (however improved technology can also be used, for example, an SLM with more pixels, which would benefit the usability of one or more embodiments of the present invention.

A DMD can be selected that operates at >1 kHz, for example. However, one or more embodiments include using wavefront modifying devices, e.g., DMDs and detection systems for the frequency-shifted EM radiation (e.g. cameras) that are sufficiently fast to perform the steps 300-308 within 1.5 seconds, or within the time the time for scatterer position shifts in the sample 244.

The detector in the detection system 216 can comprise, but is not limited to, a camera, and if a camera is used for digital detection (e.g., off axis digital holography), an example of a camera includes, but is not limited to, an sCMOS camera PCO edge (e.g., from [16]).

The apparatus further comprises one or more controllers (e.g., processors, personal computer that is sufficiently fast) 222. for (1) instructing the EM radiation source and control system to irradiate the sample with the input EM radiation having the input wavefront, (2) receiving the amount of the frequency shifted EM radiation from the detection system, (3) controlling how the wavefront modifying device modifies the input wavefront into the modified wavefront using the feedback (e.g., raster scanning the position of the pixels so that the phase of the input EM radiation is cycled from 0 to $2\pi$ as described in Block 306), wherein the modified wavefront is used as the input wavefront, and (4) repeating functions (1)-(3) sequentially until a threshold intensity or desired focus of the input EM radiation at the target is achieved. The one or more controllers can select the modified wavefront that maintains, increases, or maximizes the amount of the frequency shifted EM radiation as compared to the amount of the frequency shifted EM radiation obtained using the input wavefront prior to the modification.

One or more embodiments of the present invention use software, including but not limited to, Matlab, Labview, Python, C++ to control the SLM, where the SLM is effectively used as a second display. One example of such a code is "fullscreen.m" [17].

The controller 222 can control or select a number of incidences of the input EM radiation 208 on the sample 204 until the desired input wavefront is achieved, for example, until a desired focus or intensity of the input EM radiation at the target is obtained (e.g., the intensity and/or focusing of the input EM radiation at the target, produced at the next incidence, is increased as compared to an intensity or focusing of the input EM radiation at the target produced by one or more of the previous incidences or prior to the modification).

The modified wavefront can form modified input EM radiation that is used as the input EM radiation in the next incidence or irradiation 302. The modified input EM radiation typically has one or more electric field amplitudes and/or phases that enable the increased intensity or increased focusing at the target, and typically has a wavefront that is scattered less by the sample.

The apparatus can further comprise a sample holder 224 for the sample (e.g., for the sample that is biological tissue 204), wherein the sample holder is adjustably positioned relative to, and radiatively coupled to, the EM radiation source 220 and control system, adjustably positioned relative to, and acoustically coupled to, the acoustic wave source (UST) and control system, and radiatively coupled to the detection system 216.

One or more translation stages can be attached to the sample holder 224 and/or the EM radiation source 220 and/or the acoustic wave source UST to enable the adjustable positioning. The position of the sample holder 224 relative to the EM source 220 can be controlled independently of the position of the sample holder 246 relative to the UST. However, a sample holder is not required (for example, when the sample is part of a human body).

For example, the sample holder can be adjustably positioned to cut the tissue 204 at the target, wherein the target is at a depth of at least 5 mm from a surface of the tissue (for example).

The acoustic wave source (UST) and control system can comprise an ultrasound transducer that generates the acoustic field comprising ultrasound that is focused to an ultrasound focus at the target, wherein the ultrasound focal spots have a diameter of 100 micrometers or less at a depth of at least 5 mm within the tissue and the input EM radiation is focused to at most a same size as the ultrasound focal spot.

The apparatus can form part of/or be coupled to/integrated with/coupled to and separate from an application system 248, wherein the application system comprises a system that uses the input EM radiation as its EM radiation source, as described in Block 310. For example, the application system can comprise a Raman Spectroscopy system. In another example, the application system can comprise a system for performing photodynamic therapy (PDT).

Advantages and Improvements

There are advantages of using ultrasound modulation rather than fluorescence as feedback. As noted above, the fluorescence feedback method requires a single small area of fluorophores at (or within the immediate vicinity of) a known targeted location, which is practically impossible for biomedical applications. Also, since fluorophores bleach fairly quickly, using a fluorophore also limits the SLM controls that can be used/experiment time that can practically be performed. However, using ultrasound modulation as feedback, longer wavelengths that will not excite fluorophores can be used. Thus, fluorophore bleaching will not be an issue, and more importantly this makes multiphoton imaging possible. The possibility of performing multiphoton imaging further improves the signal to background ratio in a sample with rather diffuse distribution of fluorophores.

Besides imaging, the ability to freely create a focus in tissues, even living tissues, opens up vast possibilities in applying current optical methods in deep tissues. For example, localized Raman spectroscopy can be performed in deep tissue, deep tissue incisions can be made without cutting through the superficial tissues, localized PDT, and localized minimally invasive deep brain neural stimulation may eventually become possible using embodiments of the present invention.

Hardware Environment

Figure 4:
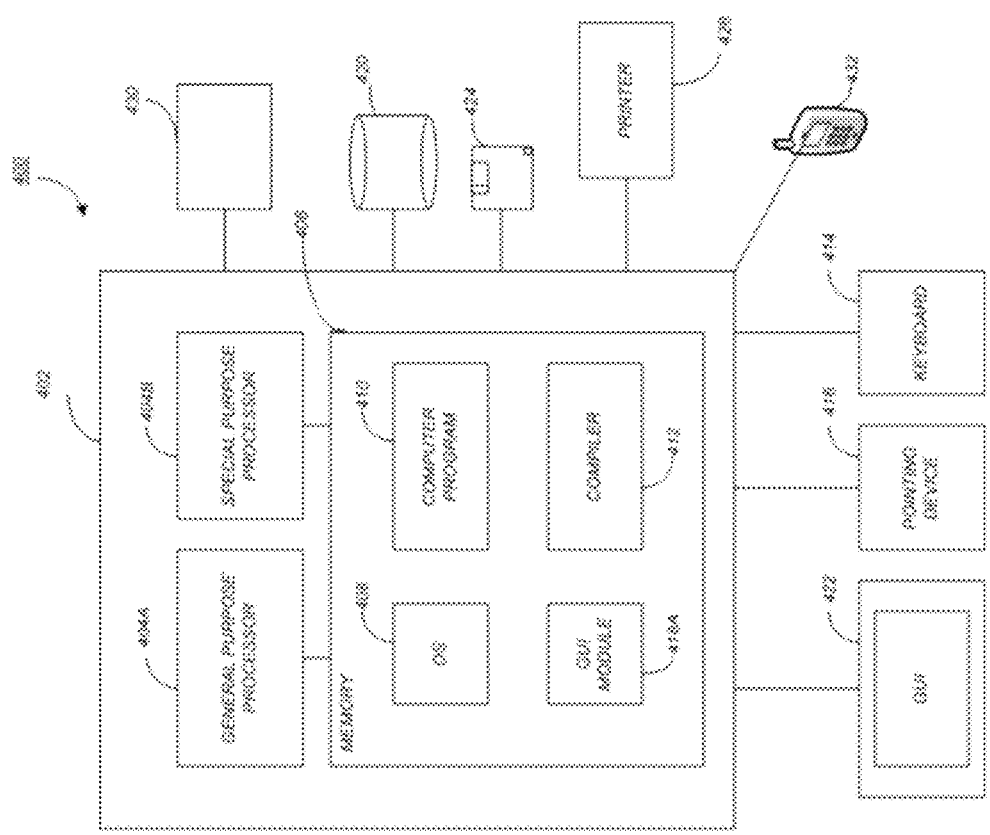
FIG. 4 is an exemplary hardware and software environment used to implement one or more embodiments of the invention.

FIG. 4 is an exemplary hardware and software environment 400 that may be used in the controllers 222 to implement one or more embodiments of the invention. The hardware and software environment includes a computer 402 and may include peripherals. Computer 402 may be a user/client computer, server computer, or may be a database computer. The computer 402 comprises a general purpose hardware processor 404A and/or a special purpose hardware processor 404B (hereinafter alternatively collectively referred to as processor 404) and a memory 406, such as random access memory (RAM). The computer 402 may be coupled to other devices, including input/output (I/O) devices such as a keyboard 414, a cursor control device 416 (e.g., a mouse, a pointing device, pen and tablet, etc.) and a printer 428. In one or more embodiments, computer 402 may be coupled to a media viewing/listening device 432 (e.g., an MP3 player, iPod™, Nook™, portable digital video player, cellular device, personal digital assistant, etc.). In one or more embodiments, computer 402 may be coupled to a VNA, or other devices used to measure the cavity complex valued resonant frequencies.

In one embodiment, the computer 402 operates by the general purpose processor 404A performing instructions defined by the computer program 410 under control of an operating system 408. The computer program 410 and/or the operating system 408 may be stored in the memory 406 and may interface with the user and/or other devices to accept input and commands and, based on such input and commands and the instructions defined by the computer program 410 and operating system (OS) 408 to provide output and results.

Output/results may be presented on the display 422 or provided to another device for presentation or further processing or action. In one embodiment, the display 422 comprises a liquid crystal display (LCD) having a plurality of separately addressable liquid crystals. Each liquid crystal of the display 422 changes to an opaque or translucent state to form a part of the image on the display in response to the data or information generated by the processor 404 from the application of the instructions of the computer program 410 and/or operating system 408 to the input and commands. The image may be provided through a graphical user interface (GUI) module 418A. Although the GUI module 418A is depicted as a separate module, the instructions performing the GUI functions can be resident or distributed in the operating system 408, the computer program 410, or implemented with special purpose memory and processors.

Some or all of the operations performed by the computer 402 according to the computer program 410 instructions may be implemented in a special purpose processor 404B. In this embodiment, the some or all of the computer program 410 instructions may be implemented via firmware instructions stored in a read only memory (ROM), a programmable read only memory (PROM) or flash memory within the special purpose processor 404B or in memory 406. The special purpose processor 404B may also be hardwired through circuit design to perform some or all of the operations to implement the present invention. Further, the special purpose processor 404B may be a hybrid processor, which includes dedicated circuitry for performing a subset of functions, and other circuits for performing more general functions such as responding to computer program instructions. In one embodiment, the special purpose processor is an application specific integrated circuit (ASIC).

The computer 402 may also implement a compiler 412 which allows an application program 410 written in a programming language such as COBOL, Pascal, C++, FORTRAN, or other language to be translated into processor 404 readable code. After completion, the application or computer program 410 accesses and manipulates data accepted from I/O devices and stored in the memory 406 of the computer 402 using the relationships and logic that was generated using the compiler 412.

The computer 402 also optionally comprises an external communication device such as a modem, satellite link, Ethernet card, or other device for accepting input from and providing output to other computers 402.

In one embodiment, instructions implementing the operating system 408, the computer program 410, and the compiler 412 are tangibly embodied in a computer-readable medium, e.g., data storage device 420, which could include one or more fixed or removable data storage devices, such as a zip drive, floppy disc drive 424, hard drive, CD-ROM drive, tape drive, etc. Further, the operating system 408 and the computer program 410 are comprised of computer program instructions which, when accessed, read and executed by the computer 402, causes the computer 402 to perform the steps necessary to implement and/or use the present invention or to load the program of instructions into a memory, thus creating a special purpose data structure causing the computer to operate as a specially programmed computer executing the method steps described herein. Computer program 410 and/or operating instructions may also be tangibly embodied in memory 406 and/or data communications devices 430, thereby making a computer program product or article of manufacture according to the invention. As such, the terms "article of manufacture," "program storage device" and "computer program product" as used herein are intended to encompass a computer program accessible from any computer readable device or media.

Of course, those skilled in the art will recognize that any combination of the above components, or any number of different components, peripherals, and other devices, may be used with the computer 402.

Although the term "user computer" or "client computer" is referred to herein, it is understood that a user computer 402 may include portable devices such as cell phones, notebook computers, pocket computers, or any other device with suitable processing, communication, and input/output capability.

Accordingly, one or more embodiments of the present invention provide a computer readable storage medium 420, wherein the computer readable storage medium 420 is encoded with computer program instructions 410 which when accessed by the controller (comprising a computer 410) cause the computer 410 to load the program instructions 410 to a memory therein creating a special purpose data structure causing the computer 402 to operate as a specially programmed computer, executing the method of irradiating a target within a sample, comprising (1) the specially programmed computer instructing the EM radiation source and control system to irradiate the sample with the input EM radiation having the input wavefront, (2) receiving, in the specially programmed computer, the amount of the frequency shifted EM radiation from the detection system, (3) the specially programmed computer controlling how the wavefront modifying device modifies the input wavefront into the modified wavefront using the feedback, wherein the modified wavefront is used as the input wavefront, and the specially programmed computer repeating functions (1)-(3) sequentially until a threshold intensity or focus of the input EM radiation at the target is achieved, wherein the specially programmed computer selects the modified wavefront that maintains, increases, or maximizes the amount of the frequency shifted EM radiation as compared to the amount of the frequency shifted EM radiation obtained using the input wavefront.

Figure 5:
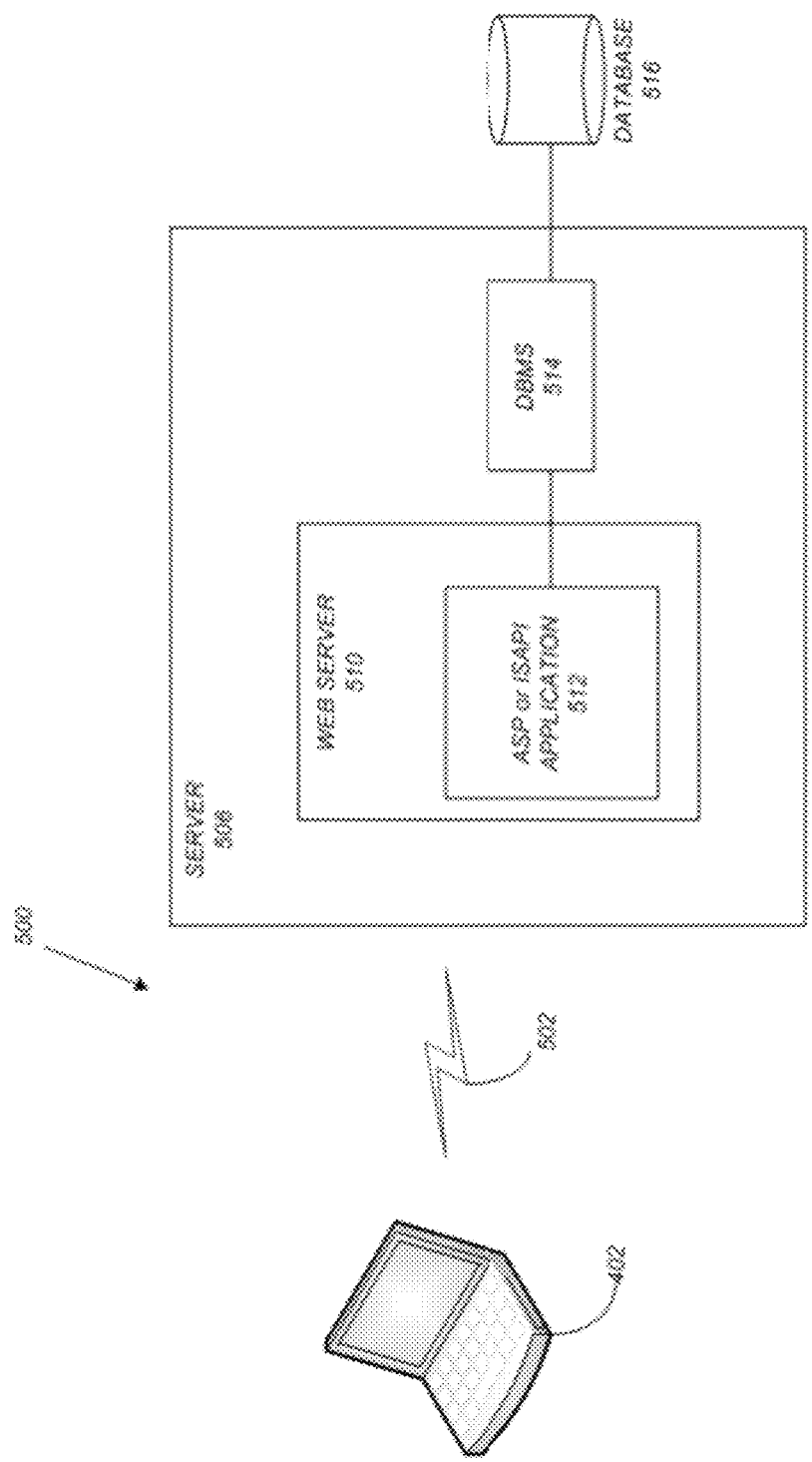
FIG. 5 schematically illustrates a typical distributed computer system using a network to connect client computers to server computers, used to implement one or more embodiments of the present invention.

FIG. 5 schematically illustrates a typical distributed computer system 500 using a network 502 to connect client computers 402 to server computers 506. A typical combination of resources may include a network 502 comprising the Internet, LANs (local area networks), WANs (wide area networks), SNA (systems network architecture) networks, or the like, clients 402 that are personal computers or workstations, and servers 506 that are personal computers, workstations, minicomputers, or mainframes (as set forth in FIG. 4).

A network 502 such as the Internet connects clients 402 to server computers 506. Network 502 may utilize ethernet, coaxial cable, wireless communications, radio frequency (RF), etc. to connect and provide the communication between clients 402 and servers 506. Clients 402 may execute a client application or web browser and communicate with server computers 506 executing web servers 510. Such a web browser is typically a program such as MICROSOFT INTERNET EXPLORER™, MOZILLA FIREFOX™, OPERA™, APPLE SAFARI™, etc. Further, the software executing on clients 402 may be downloaded from server computer 506 to client computers 502 and installed as a plug in or ACTIVEX™ control of a web browser. Accordingly, clients 402 may utilize ACTIVEX™ components/component object model (COM) or distributed COM (DCOM) components to provide a user interface on a display of client 402. The web server 410 is typically a program such as MICROSOFT'S INTERNENT INFORMATION SERVER™.

Web server 510 may host an Active Server Page (ASP) or Internet Server Application Programming Interface (ISAPI) application 512, which may be executing scripts. The scripts invoke objects that execute business logic (referred to as business objects). The business objects then manipulate data in database 516 through a database management system (DBMS) 514. Alternatively, database 516 may be part of or connected directly to client 402 instead of communicating/obtaining the information from database 516 across network 502. When a developer encapsulates the business functionality into objects, the system may be referred to as a component object model (COM) system. Accordingly, the scripts executing on web server 510 (and/or application 512) invoke COM objects that implement the business logic. Further, server 506 may utilize MICROSOFT'S™ Transaction Server (MTS) to access required data stored in database 516 via an interface such as ADO (Active Data Objects), OLE DB (Object Linking and Embedding DataBase), or ODBC (Open DataBase Connectivity).

Generally, these components 506-516 all comprise logic and/or data that is embodied in/or retrievable from device, medium, signal, or carrier, e.g., a data storage device, a data communications device, a remote computer or device coupled to the computer via a network or via another data communications device, etc. Moreover, this logic and/or data, when read, executed, and/or interpreted, results in the steps necessary to implement and/or use the present invention being performed.

Although the term "user computer", "client computer", and/or "server computer" is referred to herein, it is understood that such computers 402 and 506 may include portable devices such as cell phones, notebook computers, pocket computers, or any other device with suitable processing, communication, and input/output capability.

Of course, those skilled in the art will recognize that any combination of the above components, or any number of different components, peripherals, and other devices, may be used with computers 402 and 506.

Software Embodiments

Embodiments of the invention are implemented as a software application on a client 402 or server computer 506.

Turbidity Suppression by Optical Phase Conjugation

One of the inventors has demonstrated turbidity suppression by optical phase conjugation and demonstrated how phase conjugate light can penetrate/transmit deep into tissues [18].

FIGS. 6(a)-(f) (from [18]) illustrate how phase conjugate light can penetrate deep into tissues for deep tissue focusing, thereby performing turbidity suppression by optical phase conjugation.

FIG. 6(a) and FIG. 6(b) illustrate an example of a set up for generating phase conjugate light to illuminate and transmit through tissue samples.

The system shown in FIGS. 6(a)-(b) employs a 532-nm Continuous Wave solid state laser 600 in a Mach-Zehnder-type interferometry scheme. The sample beam 602 and the reference beam 604 are derived/split from the output beam 606 from laser 600 using beamsplitter BS1. The sample beam 602 is scattered on transmission through the sample 608 to form scattered beam 610. The scattered beam 610 (e.g., formed from a 20-mW incident power, 2-mm collimated sample beam 602) interfered with the reference beam 604 (e.g., 10 mW), as depicted in FIG. 6(a), to form an interference pattern. Beamsplitter BS3 is used to direct the reference beam 604, and mirror M1 and beamsplitter BS2 are used to direct the sample beam 602. This interference pattern was written into a 45-deg cut iron-doped $LiNbO_3$ photorefractive crystal 612 over a time period of 20 s. A phase conjugate reference beam 614 (e.g., 2 mW), approaching the photorefractive crystal 612 from the opposite direction, was used to play back the "time-reversed" wavefront 616, as seen in FIG. 6(b). The phase conjugate reference beam 614 is formed from reference beam 604 using beamsplitter BS3, and mirrors M2, M3, and M4 are used to direct the phase conjugate reference beam 614 onto the crystal 612, thereby illuminating the interference pattern with the phase conjugate reference beam 614. The conjugate reference beam 614 interacts with the interference pattern in the photorefractive crystal 612 to produce the phase conjugate sample beam 616 (phase conjugate of the scattered beam 610). The phase conjugate wavefront or beam 616 retraced its path through the sample 608, reconstructing the incident light field of sample beam 602. The phase conjugate sample beam 616 is transmitted through the sample 608 to form a transmitted, phase conjugate, reconstructed sample beam 618 that is directed onto a Charge Coupled Device (CCD)

using beam splitter BS2, and focused onto the CCD using a lens (e.g., f=10 cm). The transmitted, phase conjugate, reconstructed sample beam 618 was then measured at a CCD camera over a variable integration time (e.g., 0.25 ms to 1 s). The CCD measures the intensity/spatial extent of the transmitted, phase conjugate, reconstructed sample beam 618.

FIG. 6(c) illustrates chicken breast tissues ($\mu_s \sim 30$ mm, wherein $\mu_s l$ is average number of scattering events, $\mu_s$ is scattering coefficient and l is path length) of varying thickness (0.25 mm, 0.55 mm, 1.0 mm, 3.0 mm, 5.0 mm, and 7.0 mm) that can be used as the sample 608 measured in FIGS. 6(a) and 6(b). FIG. 6(c) illustrates the chicken breast samples as observed with ambient non-phase conjugated light, or light having non-optimized wavefronts. The tissue sits on a background printed with the words "Caltech." For the thinner samples (0.25 mm, 0.55 mm, 1.0 mm), the word "Caltech" is visible through the samples using the sample beam. However, for tissue samples thicker than 1 mm, scattering in the sample prevents visibility of background "Caltech" through the sample using the sample beam. FIG. 6(d) illustrates one of the chicken breast samples 608 of FIG. 6(c) mounted in the setup of FIGS. 6(a) and 6(b).

FIG. 6(e) illustrates that no signal is measured on a CCD placed on the exit side of the 7 mm thick sample 608 of FIG. 6(c), when the sample 608 is illuminated with the sample beam 602 comprising non-optimized, non-tailored, non-phase conjugate light.

On the other hand, FIG. 6(f) illustrates that a strong focused signal (focal spot 620) is measured on a CCD when the 7 mm thick sample 608 of FIG. 6(c) is illuminated with the phase conjugate sample beam 616 in the setup of FIG. 6(b). FIG. 6(f) plots the magnitude of the detected transmitted, phase conjugate, reconstructed sample beam 618 as a function of axial direction across a transverse slice through the phase conjugate reconstructed beam 618, showing the focal spot 620 and focus diameter. FIG. 6(f) also illustrates that the focus diameter reduced by a factor of at least 10 and the focal depth can be 1 mm or more in tissue. However, the focal depth can be, but is not limited to, 1 mm to more than 1 cm, in tissue.

The present invention is not limited to particular types of tissue. For example, soft tissues, for example: tumors, embryos, muscle tissues, epidermis and dermis, breast tissue etc, can be used.

Figures 7A, 7B:
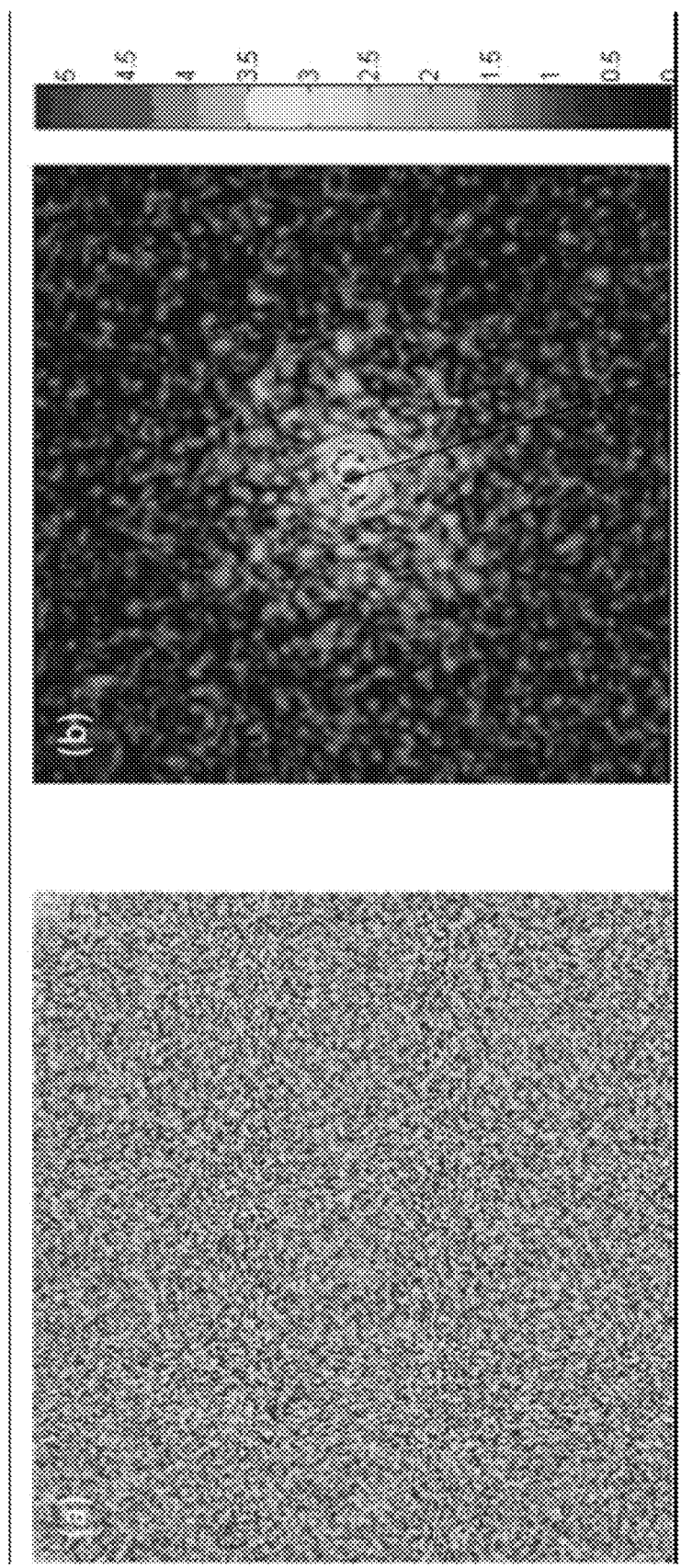

FIGS. 7(a)-(b) illustrate that an SLM can be used to produce the phase conjugate sample beam 616 and that non-biological samples can be used for non-medical applications. FIG. 7(a) shows a phase map of the speckle pattern produced when a flat wavefront is sent through a scattering medium comprising paint, and FIG. 7(b) shows that well aligned Digital Optical Phase Conjugation device (DOPC) comprising an SLM sends back a phase conjugate wavefront that results in a focused spot 700, wherein the image is displayed on logarithmic scale (see also U.S. patent application Ser. No. 12/943,857, filed on Nov. 10, 2010, by Changhuei Yang and Meng Cui, entitled "TURBIDITY SUPPRESSION BY OPTICAL PHASE CONJUGATION USING A SPATIAL LIGHT MODULATOR," which application is incorporated herein.

One or more embodiments of the present invention (see e.g., FIGS. 2(a)-(c) and 3, perform steps 300-308 to modify 306 the input wavefront/input EM radiation into a modified wavefront comprising the phase conjugate of the scattered light 210 (e.g., the input EM radiation that is scattered through the sample 204 and that interacts with the ultrasound at the ultrasound focus). The phase conjugate of the scattered light/EM radiation can then be used as the input EM radiation that illuminates the sample in a next incidence of the input EM radiation. For example, one or more embodiments of the present invention can reduce the focus diameter of the input EM radiation in the sample by a factor of at least 10, and produce a focal depth of the input EM radiation that is at least 1 mm, to more than 1 cm, in tissue (for example).

Non-biological samples can also be used, and non-medical applications can be performed using one or more embodiments of the present invention. The present invention is not limited to particular samples or applications. For example, the sample can be any turbid sample and applications can be any application where it is desired to form a focus in a turbid environment.

CONCLUSION

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

The following references are incorporated by reference herein:

[1] I. M. Vellekoop, and A. P. Mosk, "Focusing coherent light through opaque strongly scattering media," Opt. Lett. 32, 2309-2311 (2007).

[2] M. Gross, P. Goy, and M. Al-Koussa, "Shot-noise detection of ultrasound-tagged photons in ultrasound-modulated optical imaging," Optics Letters 28, 2482-2484 (2003).

[3] S. R. Kothapalli, and L. H. V. Wang, "Ultrasound-modulated optical microscopy," Journal of Biomedical Optics 13 (2008).

[4] Vellekoop I M & Mosk A P (2008) Universal Optimal Transmission of Light Through Disordered Materials. *Physical Review Letters* 101(12):120601.

[5] Cui, M., Parallel wavefront optimization method for focusing light through random scattering media, Optics Letters, Vol. 36, No. 6, Mar. 15, 2011, p. 870.

[6] Popoff, S. M. et al. Measuring the transmission matrix in optics: an approach to the study and control of light propagation in disordered media, Physical Review Letters 104, 100601 (2010), 100601.

[7] Wang F (2009) Wavefront sensing through measurements of binary aberration modes. *Appl. Opt.* 48(15): 2865-2870.

[8] Cui, M A high speed wavefront determination method based on spatial frequency modulations for focusing light through random scattering media, Optics Express Vol. 19, No. 4, p 2989 (Feb. 1, 2011).

[9] Yamaguchi I & Zhang T (1997) Phase-shifting digital holography. *Opt. Lett.* 22(16):1268-1270.

[10] Gross, M. et al. Shot-noise detection of ultrasound-tagged photons in ultrasound-modulated optical imaging, Optics Letters Vol. 28, No. 24, Dec. 15, 2003, p. 2482.

[11] Gross, M. et al. Detection of the tagged or untagged photons in acousto-optic imaging of thick highly scattering media by photorefractive adaptive holography, Eur. Phys. J. E 28, 173-182 (2009).

[12] Sakadžic S. and Wang L. V. High-resolution ultrasound-modulated optical tomography in biological tissue reference for the confocal Fabry-Perot detection method, Optics Letters Vol. 29, No. 23, Dec. 1, 2004, p. 2770.
[13] http://shop.olympus-ims.com/en/shop/item/269-productId.570437674_269-catId.0562036984.html.
[14] Wang, L. H. V., Ultrasound-mediated biophotonic imaging: A review of acousto-optical tomography and photo-acoustic tomography. Disease Markers, 2003. 19(2-3): p. 123-138.
[15] http://www.newport.com/navigator.
[16] http://www.pco.de.
[17] http://www.mathworks.com/matlabcentral/fileexchage/11112
[18] McDowell E J, et al. (March/April 2010) Turbidity suppression from the ballistic to the diffusive regime in biological tissues using optical phase conjugation. *Journal of Biomedical Optics* 15(2), 025004.

What is claimed is:

1. A method for irradiating a target within a scattering medium, comprising:
   (a) controllably defining a target within a scattering medium with an acoustic field transmitted from an acoustic wave source;
   (b) transmitting input electromagnetic (EM) radiation from pixels of a wavefront modifying device to the scattering medium, including the target, wherein:
      the input EM radiation irradiating the target has an input wavefront and a frequency, and
      at least some of the input EM radiation that passes through the acoustic field at the target is shifted in frequency by the acoustic field and outputs from the scattering medium as output EM radiation comprising frequency shifted EM radiation;
   (c) detecting an amount of the frequency shifted EM radiation; and
   (d) modulating the pixels, wherein:
      the modulating of the pixels iteratively modifies a phase, or amplitude, or the phase and the amplitude of the input wavefront, using feedback comprising the amount of the frequency shifted EM radiation that is detected and so as to increase the amount of the frequency shifted EM radiation that is detected.

2. The method of claim 1, further comprising modulating the pixels until a maximum amount of the frequency shifted EM radiation is detected.

3. The method of claim 1, wherein the acoustic field is focused to produce a first focus of the acoustic field at the target, and the modulating of the pixels forms a modified wavefront converging to form a second focus of the input EM radiation at the target.

4. The method of claim 3, further comprising using the input EM radiation comprising the modified wavefront to perform Raman spectroscopy of the target.

5. The method of claim 3, wherein:
   the scattering medium comprises at least one biological medium comprising biological cells, or biological tissue, or biological cells and biological tissue, and
   the input EM radiation does not damage the biological medium that is not at the target, and
   further comprising using the input EM radiation, comprising the modified wavefront, to cut the biological medium at, and defined by, the target, wherein the target is at a depth of no less than 1 mm from a surface of the biological medium.

6. The method of claim 2, wherein:
   the scattering medium comprises at least one biological medium comprising biological cells, or biological tissue, or biological cells and biological tissue,
   the acoustic field comprises ultrasound that is focused to an ultrasound focal spot at the target,
   the ultrasound focal spot has a diameter of 100 micrometers or less at a depth of no less than 5 mm within the biological medium, and
   the input EM radiation having the modified wavefront is focused to at most a same size as the ultrasound focal spot.

7. The method of claim 3, further comprising:
   performing photodynamic therapy on the scattering medium comprising at least one biological medium comprising biological cells, or biological tissue, or biological cells and biological tissue, wherein:
   the input EM radiation having the modified wavefront excites a photosensitive agent at the target to activate the target and trigger the photodynamic therapy of the biological medium at the target, and
   the target is at a depth of no less than 1 mm from a surface of the biological medium.

8. The method of claim 3, wherein the modified wavefront is a phase conjugate of the input wavefront.

9. The method of claim 1, wherein the acoustic field comprises ultrasound.

10. The method of claim 1, wherein the irradiating of the scattering medium includes selecting the frequency of the input EM radiation that enables multi-photon excitation of the target.

11. The method of claim 1, further comprising performing steps (a)-(d) within 1.5 seconds.

12. The method of claim 11, wherein:
    the scattering medium comprises at least one biological medium comprising biological tissue, or biological cells, or biological tissue and biological cells.

13. The method of claim 1, wherein the pixels are modulated by (1) raster scanning, (2) frequency modulation, or (3) according to a matrix, a combination of (2) and (3), or a combination of (1) and (2).

14. An apparatus implementing the method of claim 1, comprising:
    a laser for irradiating the scattering medium with the input Electromagnetic (EM) radiation;
    a detection system for detecting an amount of the frequency shifted EM radiation; and
    the wavefront modifying device chosen from a deformable mirror device and a spatial light modulator.

15. An apparatus for irradiating a target within a scattering medium, comprising:
    a detector detecting modulated electromagnetic (EM) radiation from a target in a scattering medium after input EM radiation from an EM radiation source is incident on the target, the input EM radiation comprising a wavefront;
    a spatial light modulator iteratively modifying a phase, or amplitude, or phase and amplitude of the wavefront incident on the target; and
    one or more processors for controlling the modifying using feedback comprising an amount of the modulated EM radiation that is detected and so as to increase the amount of the modulated EM radiation that is detected.

16. The apparatus of claim 15, wherein the one or more processors select the wavefront comprising a modified wavefront that maximizes the amount of the modulated EM radiation as compared to the amount of the modulated EM radiation obtained using the wavefront prior to the modifying.

17. The apparatus of claim 15, further comprising an acoustic wave source and control system focusing an acoustic field at the target, wherein the acoustic field modulates the input EM radiation into the modulated EM radiation and the wavefront converges to form a focus of the input EM radiation at the target.

18. The apparatus of claim 17, wherein the acoustic wave source comprises an ultrasound transducer, the acoustic field comprises ultrasound, the EM radiation source comprises a laser, and the detector comprises a camera and interferometer.

19. The apparatus of claim 17, further comprising a scattering medium holder for the scattering medium that comprises at least one biological medium comprising biological cells, or biological tissue, or biological cells and biological tissue, wherein the scattering medium holder is:
   adjustably positioned relative to the EM radiation source;
   adjustably positioned relative to the acoustic wave source; and
   coupled to the detector.

20. The apparatus of claim 19, wherein:
   the scattering medium holder is adjustably positioned relative to the acoustic wave source and the EM radiation source, to cut the biological medium at the target, and
   the target is at a depth of no less than 1 mm from a surface of the tissue.

21. The apparatus of claim 19, wherein:
   the acoustic wave source comprises an ultrasound transducer that generates the acoustic field comprising ultrasound that is focused to an ultrasound focal spot at the target;
   the ultrasound focal spot has a diameter of 100 micrometers or less at a depth of no less than 5 mm within the biological medium; and
   the input EM radiation is focused to at most a same size as the ultrasound focal spot.

22. The apparatus of claim 19, wherein:
   the input EM radiation having the wavefront comprising a modified wavefront modified by the spatial light modulator excites a photosensitive agent at the target, thereby activating the target.

23. The apparatus of claim 15, wherein the apparatus is optically coupled to a Raman spectroscopy system and the input EM radiation is used to perform Raman spectroscopy of the target.

24. The apparatus of claim 15, wherein the EM radiation source irradiates the scattering medium with the input EM radiation having the frequency that enables multi-photon excitation of the target.

25. A method for irradiating a target within a scattering medium with electromagnetic (EM) radiation, comprising:
   (a) receiving feedback comprising an amount of feedback Electromagnetic (EM) radiation, wherein the feedback is obtained using a process comprising:
      (i) transmitting one or more fields into a scattering medium to controllably define a target within the scattering medium, wherein the fields are scattered less than the EM radiation;
      (ii) irradiating the scattering medium, including the target, with input EM radiation having an input wavefront and a frequency;
      (iii) detecting the amount of the feedback EM radiation, wherein:
      at least some of the input EM radiation that passes through the one or more fields at the target interacts with the one or more fields and outputs from the scattering medium as output EM radiation comprising the feedback EM radiation, and
   the detecting includes:
      interfering the output EM radiation with a reference tuned to a frequency of the feedback EM radiation to form a signal, and
      measuring the signal on a detector, wherein an amplitude of the signal corresponds to the amount of the feedback EM radiation; and
   (b) digitally modifying a phase, or an amplitude, or the phase and the amplitude of the input wavefront to form a modified wavefront, using the feedback comprising the amount of the feedback EM radiation that is detected, wherein the modifying comprises:
   modulating pixels on a wavefront modifying device while irradiating the target and receiving the amount of the feedback EM radiation, so as to increase the amount of the feedback EM radiation that is detected, thereby iteratively forming the modified wavefront that is less scattered by the scattering medium as compared to the input wavefront; and
   wherein
   the modified wavefront is used as the input wavefront in the next step (a) (ii) and reduced scattering of the modified wavefront by the scattering medium increases transmittance of the frequency of the input EM radiation to the target, thereby increasing intensity and reducing focus size of the input EM radiation at the target.

* * * * *